(12) United States Patent
Arbefeuille

(10) Patent No.: US 12,171,651 B2
(45) Date of Patent: Dec. 24, 2024

(54) SYSTEM AND METHOD TO RADIALLY CONSTRICT A STENT GRAFT

(71) Applicant: Bolton Medical, Inc., Sunrise, FL (US)

(72) Inventor: Samuel Arbefeuille, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 18/216,148

(22) Filed: Jun. 29, 2023

(65) Prior Publication Data

US 2023/0338133 A1 Oct. 26, 2023

Related U.S. Application Data

(63) Continuation of application No. 16/379,490, filed on Apr. 9, 2019, now Pat. No. 11,730,584, which is a
(Continued)

(51) Int. Cl.
*A61F 2/07* (2013.01)
*A61F 2/06* (2013.01)
(Continued)

(52) U.S. Cl.
CPC .................. *A61F 2/07* (2013.01); *A61F 2/89* (2013.01); *A61F 2/954* (2013.01);
(Continued)

(58) Field of Classification Search
CPC ...... A61F 2/07; A61F 2/89; A61F 2/95; A61F 2/954; A61F 2002/061; A61F 2002/075; A61F 2220/0075
(Continued)

(56) References Cited

U.S. PATENT DOCUMENTS

| 5,242,452 A | 9/1993 | Inoue |
| 5,507,769 A | 4/1996 | Marin et al. |

(Continued)

FOREIGN PATENT DOCUMENTS

| AU | 2016256777 B1 | 4/2017 |
| CN | 102413794 A | 4/2012 |

(Continued)

OTHER PUBLICATIONS

Extended European Search Report for EP Application No. 21153107.4 dated May 18, 2021.
(Continued)

*Primary Examiner* — Kankindi Rwego
(74) *Attorney, Agent, or Firm* — Stephen J. Kenny; Foley Hoag LLP

(57) ABSTRACT

A stent graft system including a component having longitudinally extending outer surface and inner surface, the inner surface defining a lumen having a longitudinal axis, a plurality of stents distributed longitudinally along the component, and a plurality of suture loops, each suture loop attached to the inner outer surface, of the stent graft, a first suture loop spaced laterally and longitudinally relative to an adjacent suture loop when the component is in an expanded configuration, the plurality of suture loops aligned longitudinally along the stent graft when the stent graft is in a radially constricted configuration, at least one ligature having a proximal end and a distal end, the ligature extending through at least some of the plurality of suture loops, whereby tension on the at least one ligature longitudinally aligns the suture loops along the longitudinal axis of the component, thereby at least partially radially constricting the stent graft.

15 Claims, 16 Drawing Sheets

Related U.S. Application Data continuation of application No. PCT/US2018/019344, filed on Feb. 23, 2018.

(60) Provisional application No. 62/463,031, filed on Feb. 24, 2017.

(51) Int. Cl.
  *A61F 2/89* (2013.01)
  *A61F 2/954* (2013.01)

(52) U.S. Cl.
  CPC ... *A61F 2002/061* (2013.01); *A61F 2002/075* (2013.01); *A61F 2220/0075* (2013.01)

(58) Field of Classification Search
  USPC ........................................................ 623/1.11
  See application file for complete search history.

(56) References Cited

U.S. PATENT DOCUMENTS

| | | | |
|---|---|---|---|
| 5,713,948 A | 2/1998 | Uflacker | |
| 5,873,906 A | 2/1999 | Lau et al. | |
| 6,280,464 B1 | 8/2001 | Hayashi | |
| 6,776,791 B1 | 8/2004 | Stallings et al. | |
| 7,435,253 B1 | 10/2008 | Hartley et al. | |
| 7,763,063 B2 | 7/2010 | Arbefeuille et al. | |
| 8,007,605 B2 | 8/2011 | Arbefeuille et al. | |
| 8,137,393 B2 | 3/2012 | Ishimaru et al. | |
| 8,172,895 B2 | 5/2012 | Anderson et al. | |
| 8,236,040 B2 | 8/2012 | Mayberry et al. | |
| 8,486,129 B2 | 7/2013 | Lautherjung | |
| 8,500,792 B2 | 8/2013 | Berra | |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,226,814 B2 | 1/2016 | Jensen et al. | |
| 9,278,018 B2 | 3/2016 | Roeder | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 9,913,743 B2 | 3/2018 | Arbefeuille et al. | |
| 10,005,269 B2 | 6/2018 | Hall et al. | |
| 10,080,674 B2 | 9/2018 | Yuan et al. | |
| 10,292,850 B2 | 5/2019 | Vad et al. | |
| 10,299,951 B2 | 5/2019 | Arbefeuille et al. | |
| 10,390,930 B2 | 8/2019 | Arbefeuille et al. | |
| 10,478,320 B2 | 11/2019 | Shahriari | |
| 10,617,542 B2 | 4/2020 | Chakfe et al. | |
| 10,898,357 B2 | 1/2021 | Arbefeuille et al. | |
| 11,219,540 B2 | 1/2022 | Arbefeuille | |
| 11,291,572 B2 | 4/2022 | Garcia | |
| 11,376,145 B2 | 7/2022 | Arbefeuille et al. | |
| 11,491,003 B2 | 11/2022 | Arbefeuille et al. | |
| 11,730,584 B2 | 8/2023 | Arbefeuille | |
| 11,744,722 B2 | 9/2023 | Garcia | |
| 2002/0038144 A1 | 3/2002 | Trout et al. | |
| 2002/0062133 A1 | 5/2002 | Gilson et al. | |
| 2002/0151956 A1 | 10/2002 | Chobotov et al. | |
| 2003/0233140 A1 | 12/2003 | Hartley et al. | |
| 2004/0073289 A1 | 4/2004 | Hartley | |
| 2005/0049674 A1 | 3/2005 | Berra et al. | |
| 2005/0119722 A1 | 6/2005 | Styrc et al. | |
| 2005/0154444 A1 | 7/2005 | Quadri | |
| 2006/0004433 A1 | 1/2006 | Greenberg et al. | |
| 2006/0015171 A1 | 1/2006 | Armstrong | |
| 2006/0020319 A1 | 1/2006 | Kim et al. | |
| 2006/0184226 A1 | 8/2006 | Austin | |
| 2007/0043425 A1 | 2/2007 | Hartley et al. | |
| 2007/0213805 A1 | 9/2007 | Schaeffer et al. | |
| 2007/0233223 A1 | 10/2007 | Styrc | |
| 2008/0082154 A1 | 4/2008 | Tseng et al. |
| 2008/0132988 A1 | 6/2008 | Jordan |
| 2008/0294234 A1 | 11/2008 | Hartley et al. |
| 2009/0248135 A1 | 10/2009 | Bruszewski et al. |
| 2010/0114290 A1 | 5/2010 | Rasmussen et al. |
| 2010/0234932 A1 | 9/2010 | Arbefeuille et al. |
| 2010/0268319 A1 | 10/2010 | Bruszewski et al. |
| 2011/0190862 A1 | 8/2011 | Bashiri et al. |
| 2012/0172965 A1 | 7/2012 | Kratzberg et al. |
| 2012/0323302 A1 | 12/2012 | Brinser |
| 2013/0116773 A1 | 5/2013 | Roeder et al. |
| 2013/0158648 A1 | 6/2013 | Hartley et al. |
| 2013/0289713 A1 | 10/2013 | Pearson et al. |
| 2014/0046429 A1 | 2/2014 | Cragg et al. |
| 2014/0180378 A1 | 6/2014 | Roeder |
| 2014/0336745 A1 | 11/2014 | Barthold et al. |
| 2015/0051691 A1 | 2/2015 | Zukowski et al. |
| 2015/0105819 A1 | 4/2015 | Becking et al. |
| 2015/0105849 A1 | 4/2015 | Cohen et al. |
| 2015/0202065 A1 | 7/2015 | Shalev et al. |
| 2015/0265444 A1 | 9/2015 | Kitaoka |
| 2016/0120667 A1 | 5/2016 | Bolduc et al. |
| 2016/0250050 A1 | 9/2016 | Lim et al. |
| 2016/0278910 A1 | 9/2016 | Kelly |
| 2016/0302950 A1 | 10/2016 | Marmur et al. |
| 2017/0281382 A1 | 10/2017 | Lostetter et al. |
| 2019/0231514 A1 | 8/2019 | Arbefeuille |
| 2019/0231568 A1 | 8/2019 | Garcia |
| 2019/0269498 A1 | 9/2019 | Arbefeuille et al. |
| 2019/0269537 A1 | 9/2019 | Arbefeuille |
| 2019/0321207 A1 | 10/2019 | Arbefeuille et al. |
| 2019/0350694 A1 | 11/2019 | Arbefeuille et al. |
| 2021/0100669 A1 | 4/2021 | Arbefeuille et al. |
| 2022/0160529 A1 | 5/2022 | Arbefeuille et al. |
| 2022/0192851 A1 | 6/2022 | Garcia |
| 2022/0313464 A1 | 10/2022 | Arbefeuille et al. |
| 2023/0048537 A1 | 2/2023 | Arbefeuille et al. |

FOREIGN PATENT DOCUMENTS

| | | |
|---|---|---|
| CN | 102711664 A | 10/2012 |
| CN | 104027187 A | 9/2014 |
| CN | 104114201 A | 10/2014 |
| CN | 105832447 A | 8/2016 |
| CN | 105943213 A | 9/2016 |
| CN | 106344208 A | 1/2017 |
| DE | 102012101103 B3 | 7/2013 |
| EP | 2471498 A1 | 7/2012 |
| EP | 2501334 A1 | 9/2012 |
| EP | 2735283 A1 | 5/2014 |
| EP | 2740440 A2 | 6/2014 |
| EP | 2745812 A1 | 6/2014 |
| EP | 3040054 A1 | 7/2016 |
| EP | 3146993 A1 | 3/2017 |
| EP | 3187155 A1 | 7/2017 |
| EP | 3272319 A1 | 1/2018 |
| EP | 3320881 A1 | 5/2018 |
| EP | 3395302 A1 | 10/2018 |
| EP | 3733124 A1 | 11/2020 |
| GB | 2464978 A | 5/2010 |
| WO | WO-1997/03624 A1 | 2/1997 |
| WO | WO-1997/25002 A1 | 7/1997 |
| WO | WO-1997/48350 A1 | 12/1997 |
| WO | WO-2001/60285 A1 | 8/2001 |
| WO | WO-2002/083038 A2 | 10/2002 |
| WO | WO-2006/037086 A1 | 4/2006 |
| WO | WO-2007/115017 A1 | 10/2007 |
| WO | WO-2009/148594 A1 | 12/2009 |
| WO | WO-2010/105195 A2 | 9/2010 |
| WO | WO-2012/116368 A2 | 8/2012 |
| WO | WO-2012/145823 A1 | 11/2012 |
| WO | WO-2014/162306 A2 | 10/2014 |
| WO | WO-2015/070792 A1 | 5/2015 |
| WO | WO-2016/122862 A1 | 8/2016 |
| WO | WO-2017/106156 A1 | 6/2017 |
| WO | WO-2017/193331 A1 | 11/2017 |

(56) References Cited

FOREIGN PATENT DOCUMENTS

WO     WO-2018/183563 A1     10/2018
WO     WO-2019/040326 A1     2/2019

OTHER PUBLICATIONS

Extended European Search Report for EP Application No. 22150465.7 dated Jun. 30, 2022.
International Preliminary Report on Patentability for International Application No. PCT/US2018/019342 dated Aug. 27, 2019.
International Preliminary Report on Patentability for International Application No. PCT/US2018/019344 dated Aug. 27, 2019.
International Preliminary Report on Patentability for International Application No. PCT/US2018/019355 dated Aug. 27, 2019.
International Preliminary Report on Patentability for International Application No. PCT/US2018/019356 dated Aug. 27, 2019.
International Search Report and Written Opinion for International Application No. PCT/US/2018/019355 dated May 22, 2018.
International Search Report and Written Opinion for International Application No. PCT/US2018/019342 dated May 22, 2018.
International Search Report and Written Opinion for International Application No. PCT/US2018/019344 dated May 16, 2018.
International Search Report and Written Opinion for International Application No. PCT/US2018/019356 dated May 16, 2018.
International Search Report and Written Opinion for International Application No. PCT/US2018/019510 dated Jul. 11, 2018.
International Search Report and Written Opinion for International Application No. PCT/US2021/058526 dated Mar. 18, 2022.
Supplementary European Search Report for EP Application No. 21187803 dated Nov. 23, 2021.

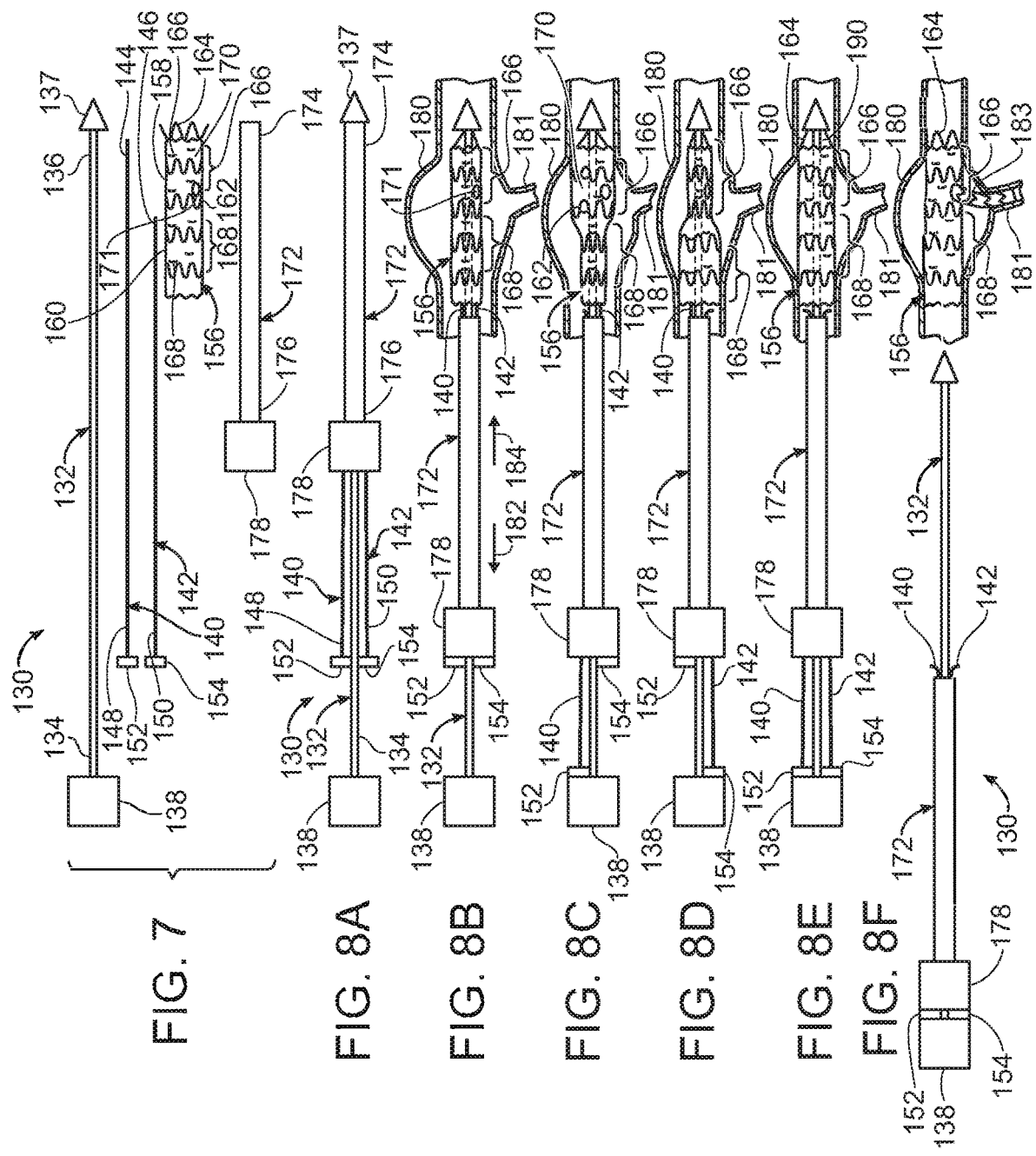

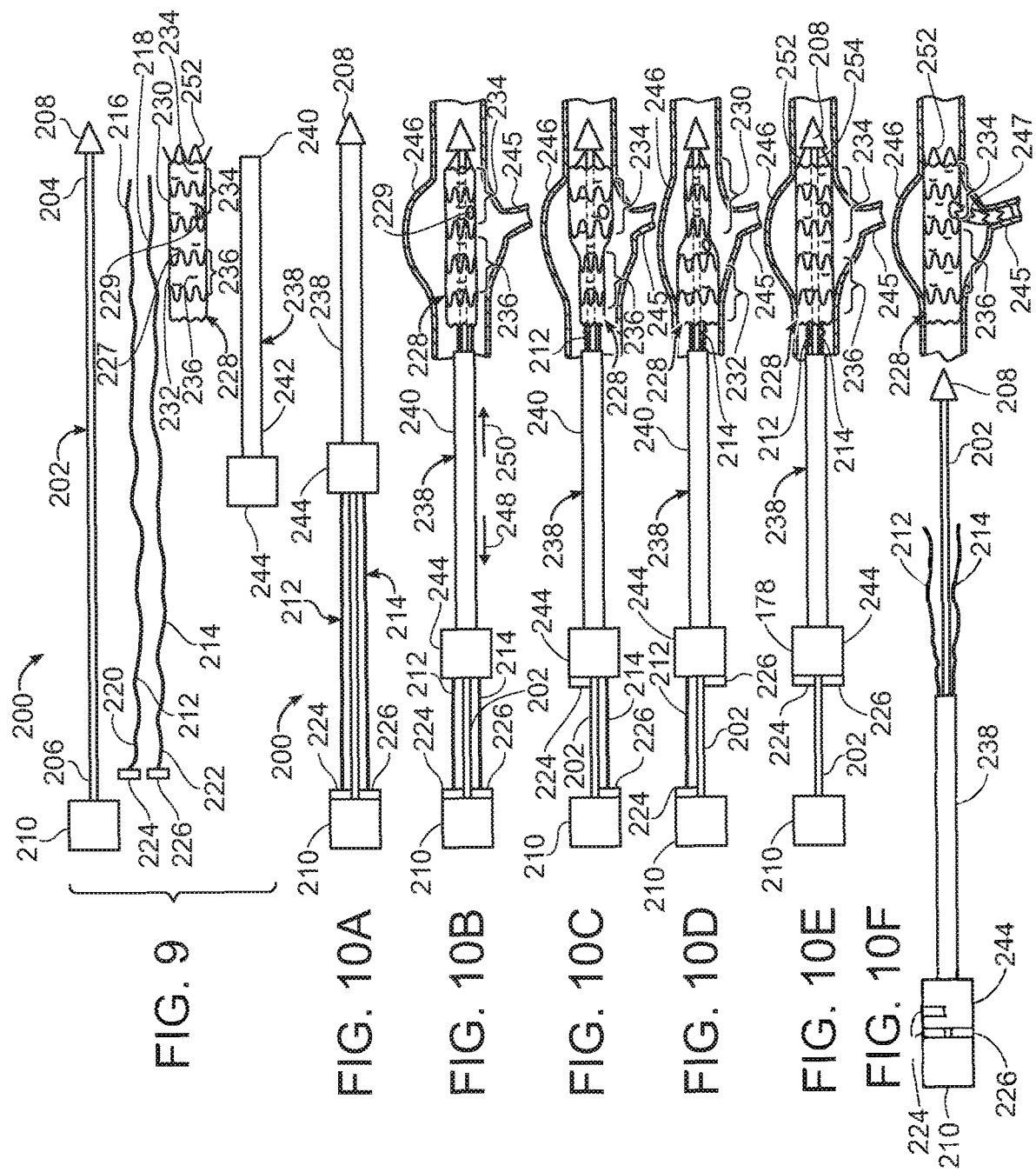

SYSTEM AND METHOD TO RADIALLY CONSTRICT A STENT GRAFT

RELATED APPLICATION

This application is a continuation of U.S. patent application Ser. No. 16/379,490, filed on Apr. 9, 2019, which was a continuation of International Application No. PCT/US2018/019344, which designated the United States and was filed on Feb. 23, 2018, published in English, which claims the benefit of U.S. Provisional Application No. 62/463,031, filed on Feb. 24, 2017. The entire teachings of the above applications are incorporated herein by reference.

BACKGROUND

Aortic pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an aortic aneurysm, an appropriate stent graft that spans the proximal and distal ends of the aneurysm to insure complete exclusion of the aneurysm sac, anchoring of the stent graft in the aorta, and minimal endoleaks. Also, endoleaks and post-surgical enlargement of the aneurysm can require additional repair to seal any expansion of the aneurysm sac, and, generally, must be done without significantly compromising blood flow through the surgical site to surrounding viscera and associated structures.

Therefore, a need exists for new and improved delivery devices, endovascular repair devices for implanting stent grafts, and methods of their use, to treat aortic pathologies, in particular aortic aneurysms.

SUMMARY

The present invention relates to stent graft systems for use in treating and repairing aortic vascular damage, such as vascular damage associated with aortic aneurysms, for example, in regions of the aorta having arterial branches to vital organs and tissues, such as, thoracic aortic aneurysms, abdominal aortic aneurysms, and thoracoabdominal aortic aneurysms, including juxtarenal aortic aneurysms and short-neck abdominal aortic aneurysms.

In one embodiment, the invention is a stent graft system that includes a stent graft having a luminal and flexible graft component defining a proximal open end, a distal open end, and having an outside surface and inside surface extending from the proximal open end to the distal open end, the inside surface defining a lumen having a longitudinal axis. The stent graft also includes a plurality of stents distributed longitudinally along the luminal flexible graft component and a plurality of suture loops spaced radially and longitudinally along the luminal flexible graft component in an arrangement that causes the stent graft to be in a radially constricted position when the suture loops are substantially aligned along the longitudinal axis of the stent graft. The stent graft system also includes at least one ligature having a proximal end and a distal end. The at least one ligature extends through the suture loops, wherein tension on the ligature or stiffness of the ligature substantially aligns the suture loops, thereby at least partially radially constricting the stent graft.

In another embodiment of the invention, a stent graft is delivered to an aneurysm site of a subject by a method that includes directing a stent graft to an aneurysm site by maintaining at least one of a plurality of stents of the stent graft in a constricted position with a ligature extending through a plurality of suture loops spaced longitudinally along a flexible luminal graft component, a luminal flexible graft component including a proximal open end, a distal open end, and outside and inside surfaces of the luminal wall extending from the proximal open end to the distal open end. The stent graft is released from the constricted position by movement of the ligature relative to the suture loops, thereby implanting the stent graft at the aneurysm site of the subject.

This invention has many advantages. For example, the physician can rotate the stent graft after it has been partially deployed, such as by only partially removing the radial constraint, or withdrawing only a portion of a plurality of radial restraints. Further, in certain embodiments, tension on a flexible ligature reversibly aligns the suture loops to thereby reversibly and radially collapse the stent graft. As a consequence, the stent graft system of the invention provides greater control relative to delivery systems that are only able to align a stent graft prior to full radial expansion of a stent graft. Accordingly, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number present in different figures represents the same item.

FIG. 6A(i) is a schematic representation of a cross section of a detail of the stent graft system of FIG. 6A taken along line 6A(i)-6A(i).

FIG. 6B(i) is a schematic representation of a cross section of a detail of the stent graft system of FIG. 6B taken along line 6B(i)-6B(i).

FIG. 7 is an exploded side view of yet another embodiment of a stent graft system of the invention.

FIG. 8A is an assembled view of the stent graft system shown in FIG. 7, wherein the stent graft shown in FIG. 7 has been loaded within an introducer sheath component of the stent graft system and, therefore, is not shown.

FIG. 8B is a side view of the stent graft system shown in FIG. 8A following direction of the stent graft to an aneurysm site of a subject in a constricted position, and following retraction of the introducer sheath of the stent graft system in a proximal direction to expose the stent graft, which is maintained in a constricted position by tension on the ligature.

FIG. 8C is a side view of the stent graft system shown in FIGS. 8A and 8B following retraction of one of two wires from suture loops distributed along a portion of the stent graft, thereby releasing the proximal portion of the stent graft from radial constriction.

FIG. 8D is a side view of the stent graft system shown in FIGS. 8A-8C following retraction of the other of the two wires from suture loops, at a distal portion of the stent graft, thereby releasing the distal portion of the stent graft from radial constriction.

FIG. 8E is a side view of the stent graft system shown in FIGS. 8A-8D following proximal retraction of both wires from the stent graft, thereby causing release from radial constriction along the entirety of the stent graft and completing delivery of the stent graft at the aneurysm site.

FIG. 8F is a side view of the stent graft system of the invention shown in FIGS. 8A-8E, following retraction of remaining portions of the stent graft system, not implanted at the aneurysm site, from the aneurysm site of the subject.

FIG. 9 is an exploded side view of another stent graft system of the invention, wherein flexible ligatures are employed rather than the semi-rigid wires of the embodiment shown in FIGS. 7 and 8A-8F.

FIG. 10A is an assembled view of the stent graft system shown in FIG. 9, wherein the stent graft shown in FIG. 9 has been loaded within an introducer sheath component of the stent graft system and, therefore, is not shown.

FIG. 10B is a side view of the stent graft system shown in FIG. 10A following direction of the stent graft to an aneurysm site of a subject and following retraction of the introducer sheath of the stent graft system in a proximal direction to expose the stent graft, which is maintained in a constricted position by tension on the flexible ligatures.

FIG. 10C is a side view of the stent graft system shown in FIGS. 10A and 10B, wherein the tension on a flexible ligature constricting a proximal portion of the stent graft has been relaxed, thereby causing the proximal portion of the stent graft to radially expand.

FIG. 10D is a side view of the stent graft delivery system shown in FIGS. 10A-10C, wherein tension has been reapplied to the flexible ligature, thereby constricting the proximal portion of the stent graft, and the flexible ligature constricting a distal portion of the stent graft has been released, thereby causing the distal portion of the stent graft to radially expand from a constricted position to an expanded position.

FIG. 10E is a side view of the stent graft system shown in FIGS. 10A-10D, wherein the flexible ligature at both the proximal and distal portions of the stent graft have been relaxed, thereby causing the entirety of the stent graft to radially expand from a constricted position to an expanded position.

FIG. 10F is a side view of the stent graft system of FIGS. 10A-10E, wherein the flexible ligatures have been released at their respective distal ends, and withdrawn from the sutures of the stent graft completing delivery of the stent graft at the aneurysm site, and wherein the remainder of the stent graft delivery system not implanted has been retracted from the aneurysm site.

DETAILED DESCRIPTION

The invention is generally directed to stent graft systems for use in treating and repairing aortic vascular damage, such as vascular damage associated with arterial aneurysms in, for example, regions of the aorta having arterial branches to vital organs and tissues, such as thoracic aortic aneurysms, abdominal aortic aneurysms and thoracoabdominal aortic aneurysms, including a juxtarenal aortic aneurysms and short-neck abdominal aortic aneurysms. The same number in different figures represents the same item.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis, also referred to herein as "vascular prosthesis," "stent graft," or "stent graft prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1A:
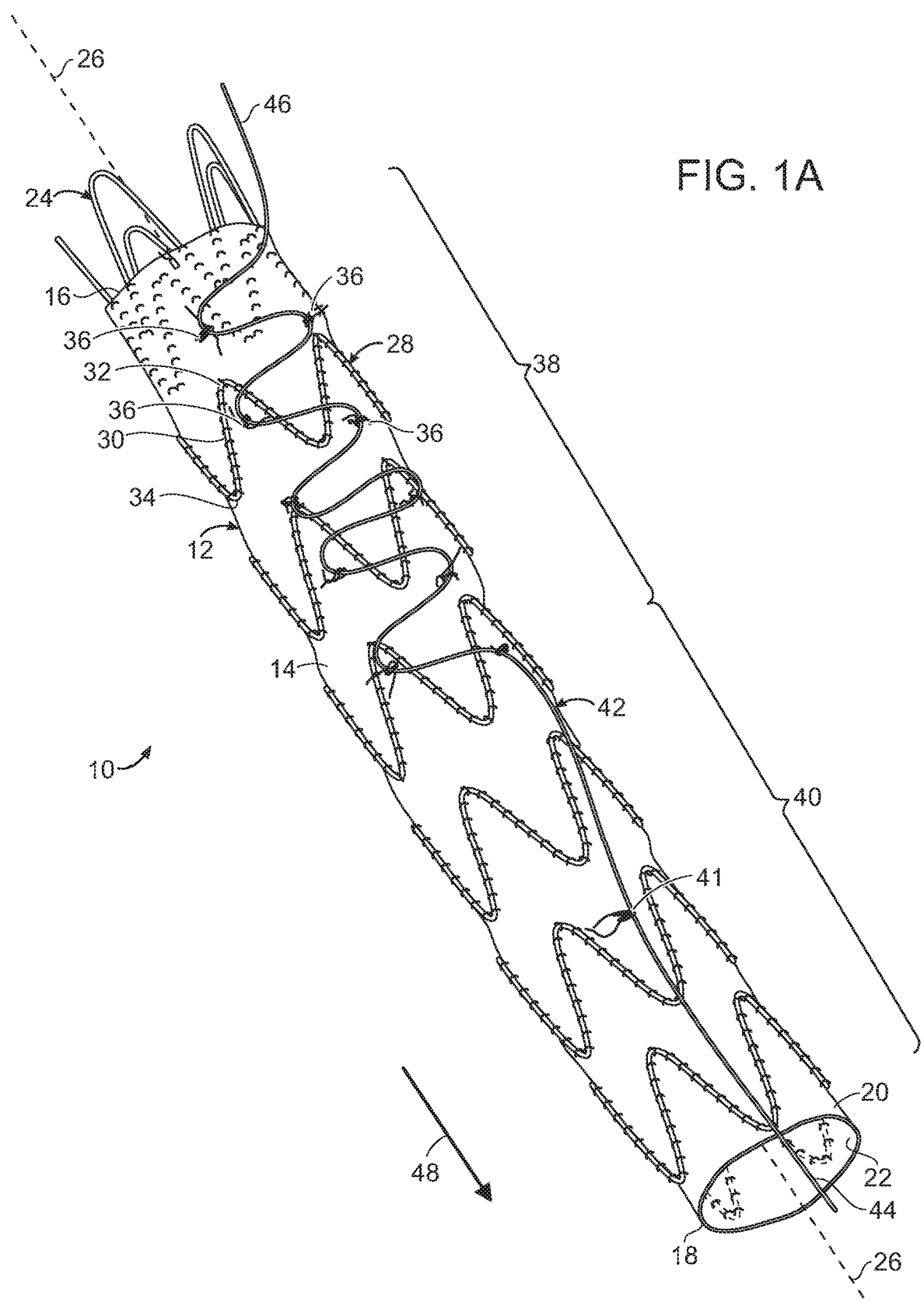
FIG. 1A is a perspective view of a stent graft system of the invention, wherein a ligature extends through suture loops at an outside surface of a stent graft.

One embodiment of a stent graft system of the invention is shown in FIG. 1A. As shown therein, stent graft system 10 includes stent graft 12. Stent graft 12 includes luminal flexible graft component 14 defining proximal open end 16 and distal open end 18. Luminal flexible graft component 14 also includes outside surface 20 and inside surface 22 extending from proximal open end 16 to distal open end 18. Inside surface 22 defines a lumen having longitudinal axis 26. Bare stent 24 is at proximal open end 16 of luminal flexible graft component 14. A plurality of stents 28 are distributed longitudinally along outside surface 20 of flexible luminal graft component 14. Stents 28 include struts 30 that define proximal apices 32 and distal apices 34, and are fixed to outside surface 20 by a suitable method, such as is known in the art, such as by use of suture thread to sew stents 28 to luminal flexible graft component.

Ligature 42 extends through suture loops 36 in longitudinal sequence along longitudinal axis 26. Stabilizing suture loop 41 is located at distal portion 40 of luminal flexible graft component 14 to stabilize ligature 42 along flexible luminal graft component 14. Ligature 42 includes proximal end 44 and distal end 46. In an embodiment, at least a portion of suture loops are between an opening of struts of a stent, referred to herein as "nested," as shown in FIG. 1A.

Figure 1B:
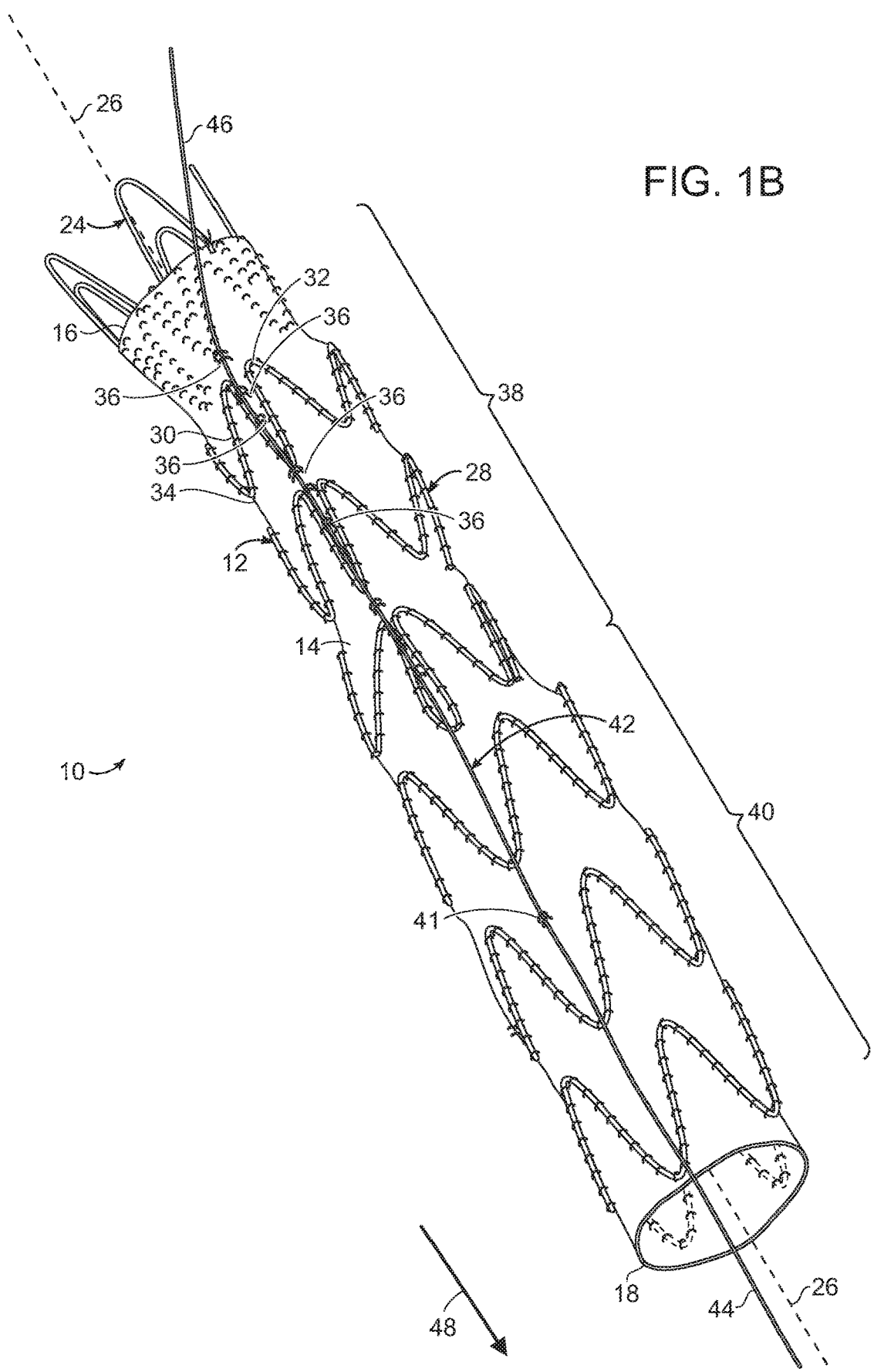
FIG. 1B is a perspective view of the stent graft system shown in FIG. 1A, but wherein the ligature is under tension, thereby causing the stent graft to be in a constricted position.

Ligature suture loops 36 are distributed along proximal portion 38 of luminal flexible graft component 14 and are distributed laterally and longitudinally relative to each other in an arrangement that causes the stent graft to be in a radially constricted position when suture loops 36 are substantially longitudinally aligned, thereby at least partially radially constricting stent graft 12, as shown in FIG. 1B. When ligature 42 is under longitudinal tension, suture loops 36 align along stent graft 12, thereby causing stents 28 and luminal flexible graft component 14 at proximal portion 38 to selectively partially radially collapse into a radially constricted position. Tension can be applied to ligature 42 by retraction of proximal end 44 by the surgeon in the direction indicated by proximal arrow 48, while distal end 46 is fixed to another component of delivery system 10, such as a nose cone (not shown). Release of tension on ligature 42 causes stents 28 to return proximal portion 38 to a radially expanded position, shown in FIG. 1A. Bare stent 24 and stents 28 are formed of a suitable material, such as is known in the art. Examples of suitable materials include stainless steel and a shape memory alloy, such as nitinol. When formed of a shape memory alloy, or certain other suitable materials, stent 28 can radially self-expand upon release from constriction by ligature 42 extending through suture loops 36. In embodiments where stents 28 are not radially self-expanding once released from radial constriction, stents 28 can be radially expanded by, for example, a balloon catheter (not shown), such as is known in the art.

Luminal flexible graft component 14 is formed of a suitable material, such as is known in the art. Examples of such materials include at least one member selected from the group consisting of polytetrafluoroethylene (PTFE), such as expanded (ePTFE), and polyethylene terephthalate (PET), such as woven polyester. Suture loops 36 are fabricated of a suitable material, such as is known in the art, including, for example polyester, nylon and polypropylene. Ligature 42 is sufficiently flexible to allow stents 28, when radially self-expanding, to radially expand in the absence of longitudinal tension on ligature 42. Examples of material suitable for use in ligature are known to those skilled in the art, such as wire, thread and cords.

Figure 2:
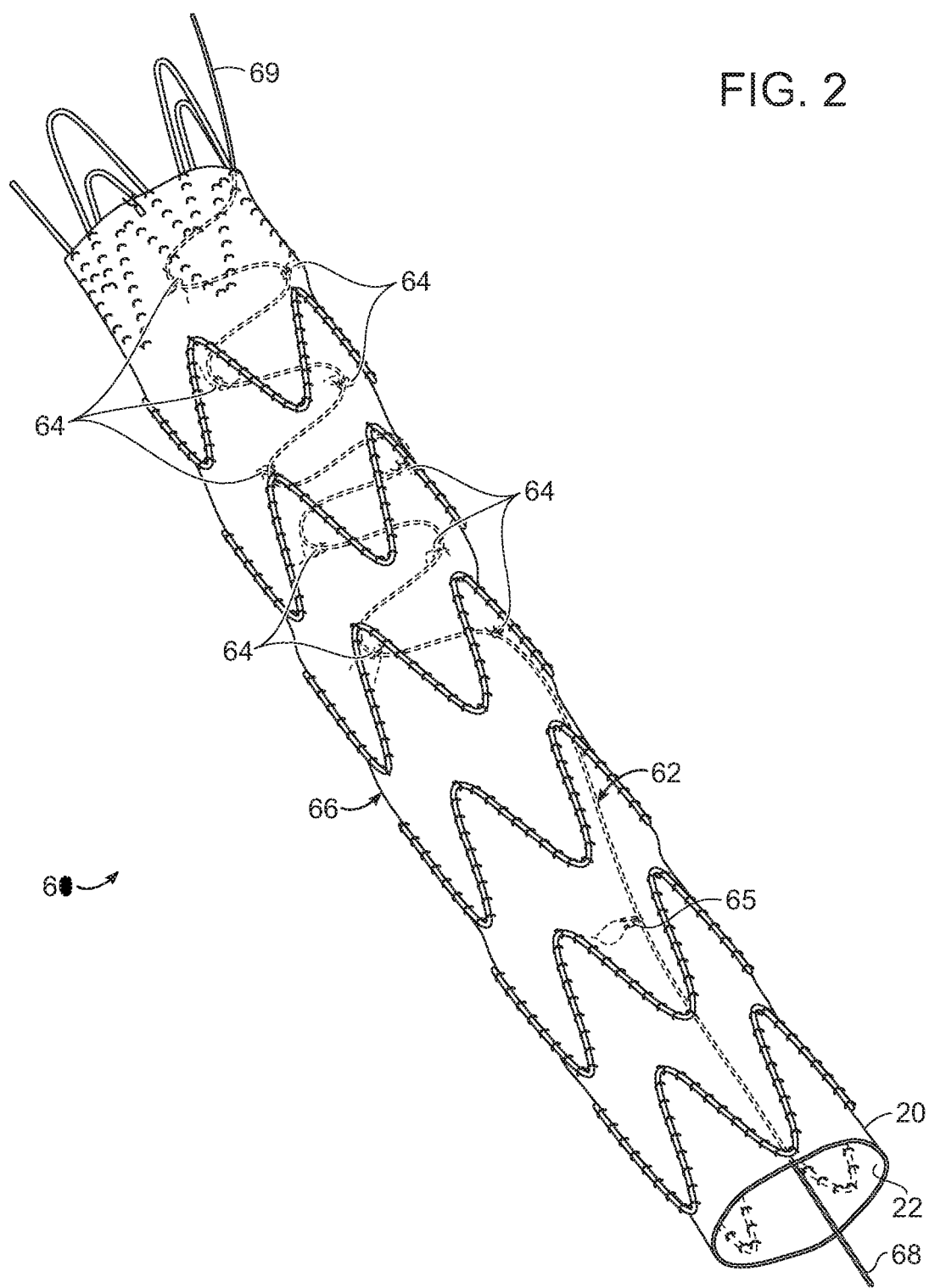
FIG. 2 is a perspective view of another embodiment of a stent graft system of the invention, wherein a ligature extends through suture loops at an inside surface of a stent graft.

In another embodiment, shown in FIG. 2, stent graft system includes ligature and sutures at inside surface 22 of stent graft 12, rather than outside surface 20, as shown in FIGS. 1A and 1B. In this embodiment, stent graft system 60 is like that of stent graft system 10, but includes ligature 62, respective suture loops 64, and stabilizing loop 65 through which ligature 62 is threaded, at inside surface 22 of luminal flexible graft component 14. As with stent graft system 10 of FIGS. 1A and 1B, radial constriction and expansion of stent graft 66 of stent graft system 60 of FIG. 2 can be achieved by applying and relaxing tension on proximal end 68 of ligature 62 while distal end 69 of ligature 62 is fixed to another component of stent graft system 60, such as a nose cone, not shown.

Figure 6A:
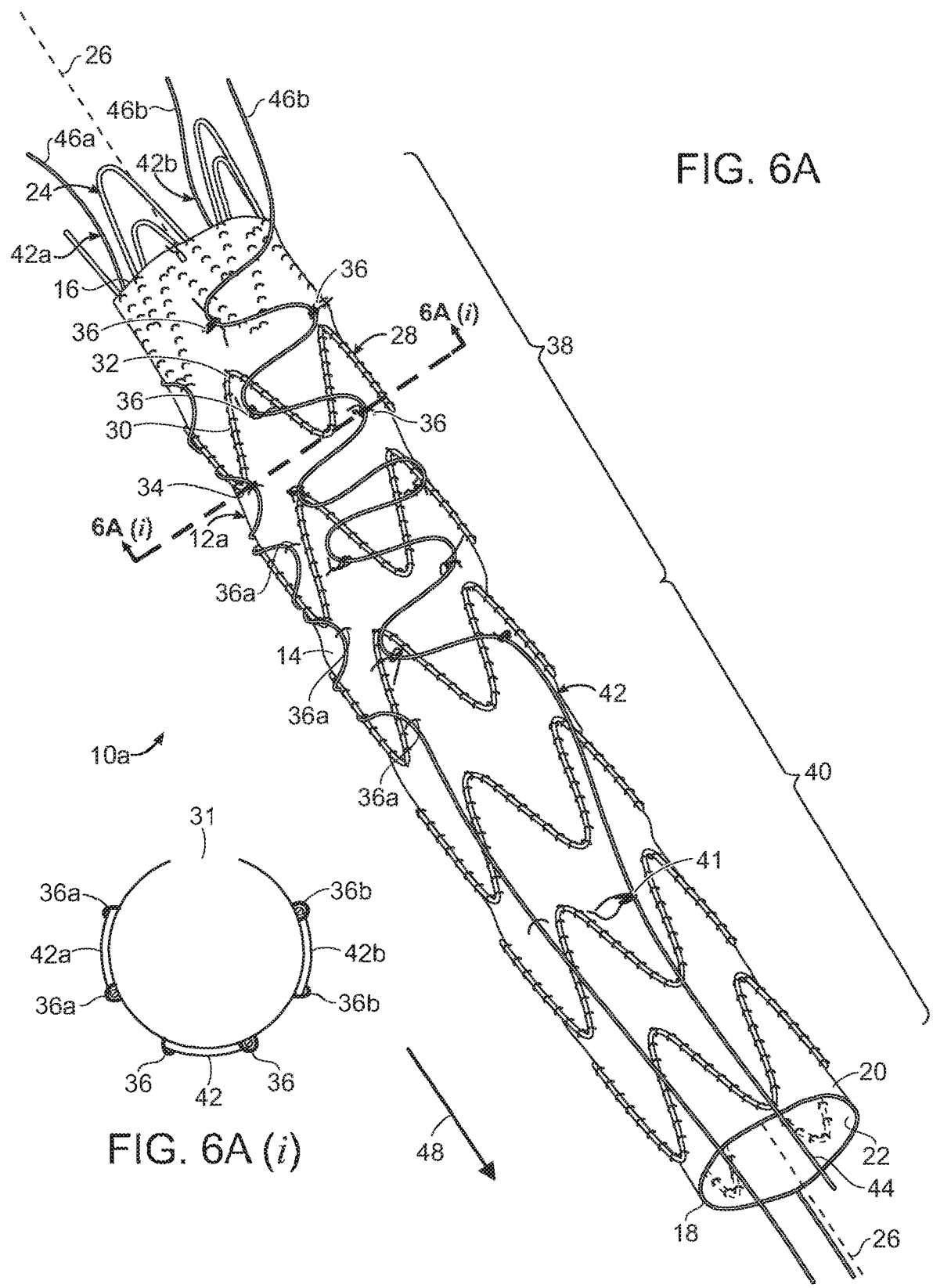
FIG. 6A is a perspective view of another embodiment of a stent graft system of the invention, wherein three ligatures extend through separate sets of suture loops distributed at the proximal portion of a stent graft.
Figure 6B:
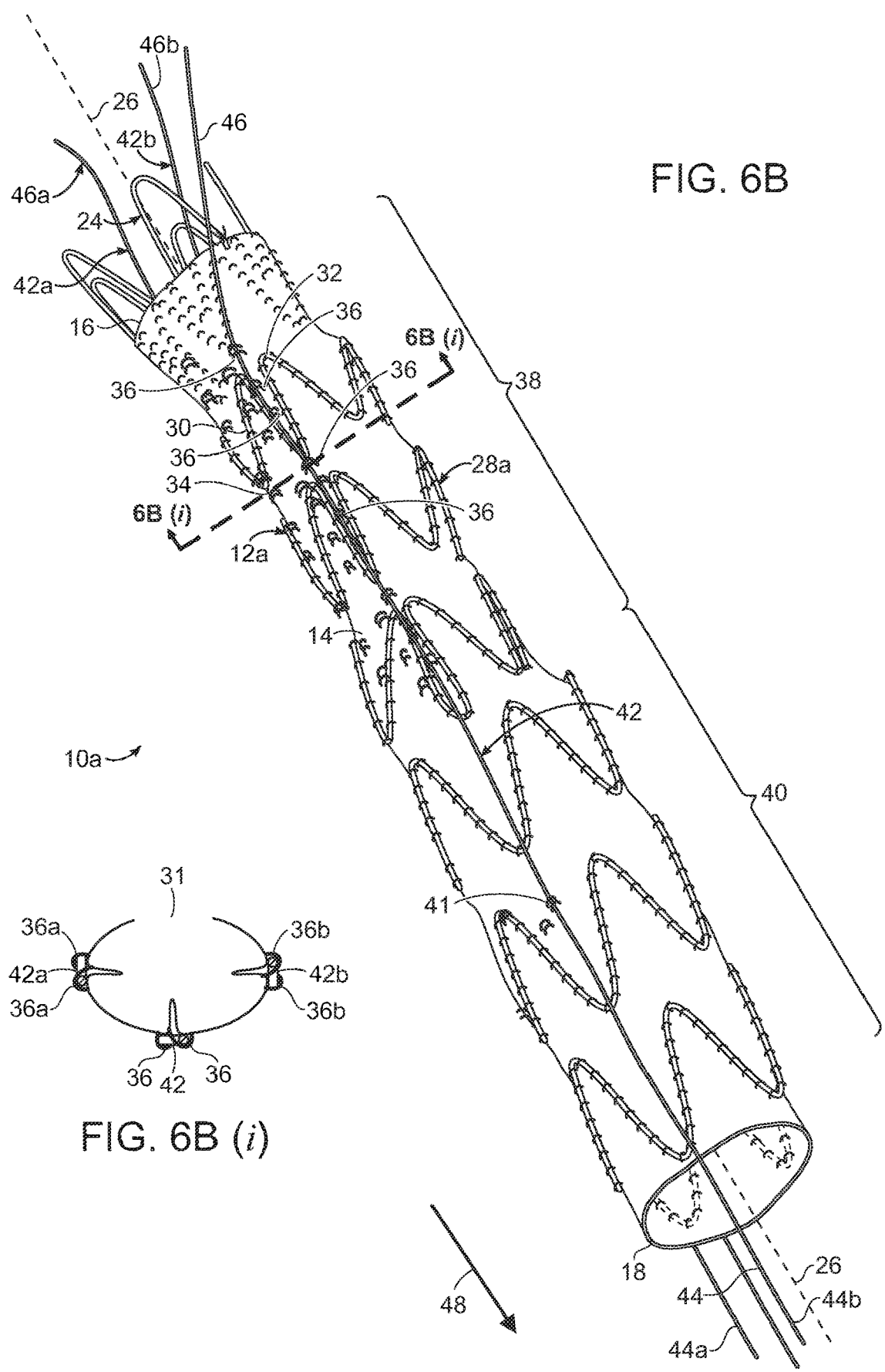
FIG. 6B is a perspective view of the stent graft system of FIG. 6A, wherein the ligatures threading suture loops at a proximal portion of the stent graft are under tension, thereby causing the proximal portion of the stent graft to be in a constricted position.

It is to be understood that additional ligatures (not shown) can be employed, along with additional distinct sets of suture loops distributed longitudinally along luminal flexible graft component. For example, the stent graft system of the invention can include three ligatures, as shown in FIGS. 6A through 6B, described below, or four ligatures (not shown). The stent graft can optionally include at least one fenestration. It is to be further understood that, in other embodiments, ligatures can, each, independently, be within or outside of luminal flexible graft component 14, and, correspondingly threaded through sets of suture loops that are at either outside surface 20 or inside surface 22 of luminal flexible graft component 14.

Figure 3A:
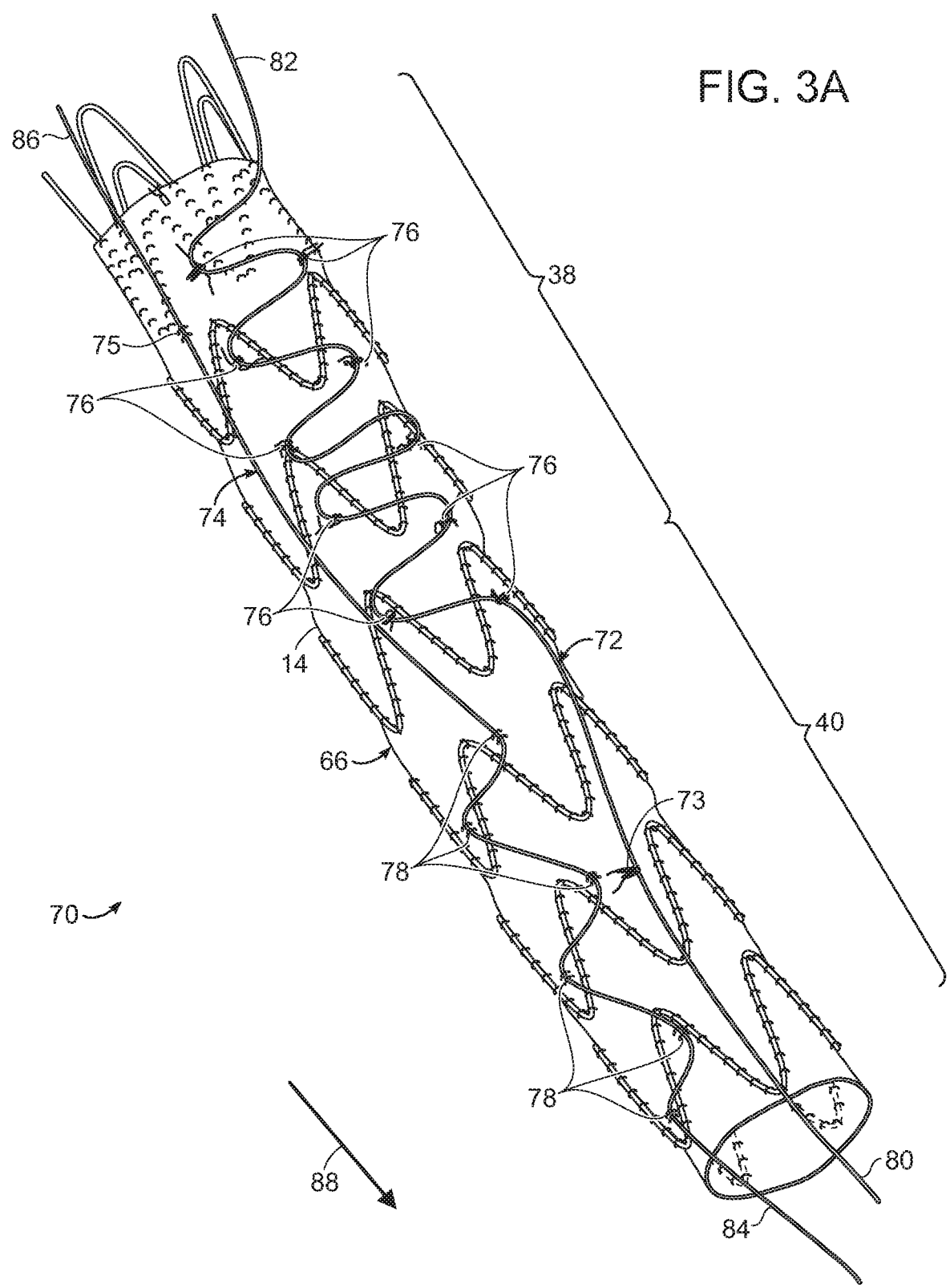
FIG. 3A is a perspective view of still another embodiment of a stent graft system of the invention, wherein two ligatures extend through separate sets of suture loops distributed at proximal and distal portions of a stent graft.

For example, in another alternative embodiment, shown in FIG. 3A, stent graft system 70 includes two ligatures 72,74, each of which is threaded through a separate set of suture loops 76,78, respectively, distributed along outside surface 20 of luminal flexible graft component 14. In this embodiment, ligature 72 extends through set of suture loops 76 predominantly distributed at proximal portion 38 of luminal flexible graft component 14, while ligature 74 extends through set of suture loops 78 distributed predominantly at distal portion 40 of luminal flexible graft component 14. Stabilizing loop 73 for ligature 72 is at distal portion 40 of flexible luminal graft component 14, while stabilizing loop 75 for ligature 74 is at proximal portion 38 of flexible luminal graft component 14.

Figure 3B:
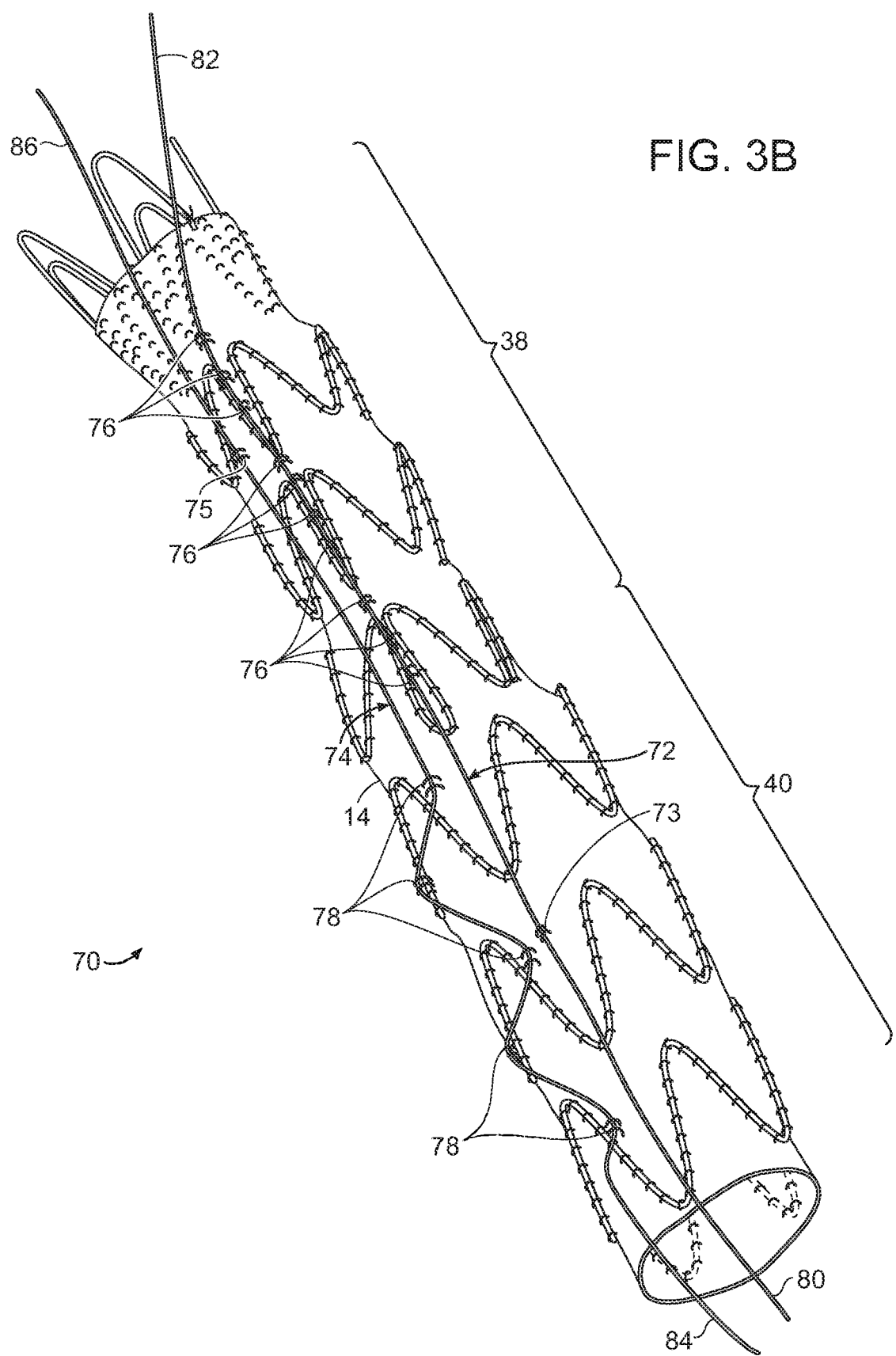
FIG. 3B is a perspective view of the stent graft system of FIG. 3A, wherein a ligature threading suture loops at a proximal portion of the stent graft is under tension, while a ligature threading suture loops at a distal portion of the stent graft is in a relaxed position.
Figure 3C:
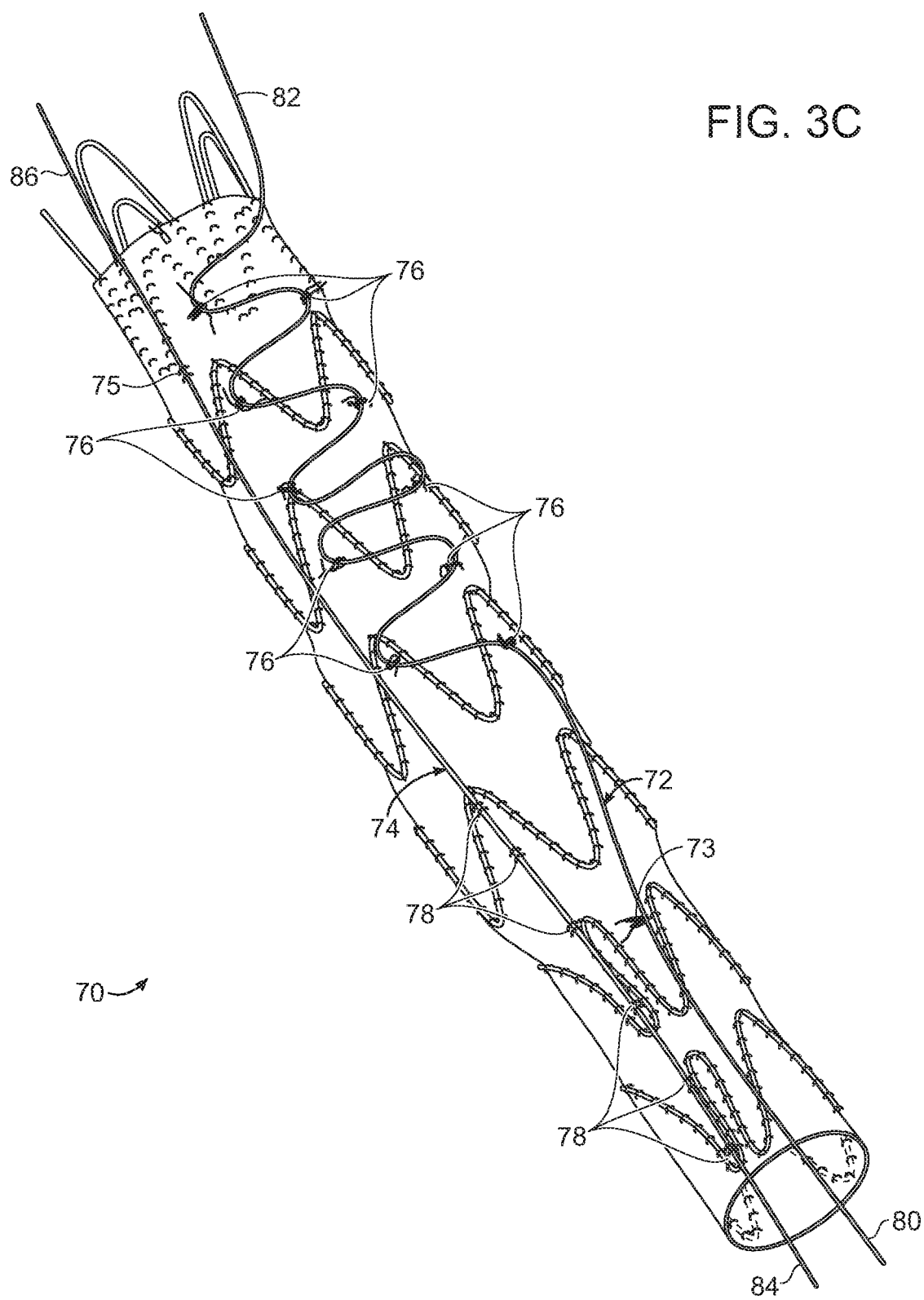
FIG. 3C is a perspective view of the stent graft system of FIGS. 3A and 3B, wherein the ligature threading suture loops at the proximal portion of the stent graft is in a relaxed position while the ligatures threading suture loops at the distal portion is under tension.

The embodiment shown in FIGS. 3A and 3B enables selective variable constriction of proximal portion 38 and distal portion 40 of luminal flexible graft component 14 by selectively and independently applying tension to ligatures 72,74 at proximal ends 80,84 of ligatures 72,74, respectively, in a proximal direction indicated by arrow 88, while distal ends 82,86 of ligatures 72,74, respectively, are fixed to another component of stent graft system 70, such as a nose cone (not shown). Specifically, as can be seen in FIG. 3B, ligature 72 is under tension, while ligature 74 is not under tension, thereby causing selective radial constriction of proximal portion 38 of luminal flexible graft component 14 by forcing longitudinal alignment of proximal suture loops 76. Conversely, and as shown in FIG. 3C, ligature 74 is under tension, while ligature 72 is not under tension, thereby causing luminal flexible graft component to be selectively radially constricted at distal portion 40 of luminal flexible graft component 14 by forced alignment of distal suture loops 78.

Figure 4A:
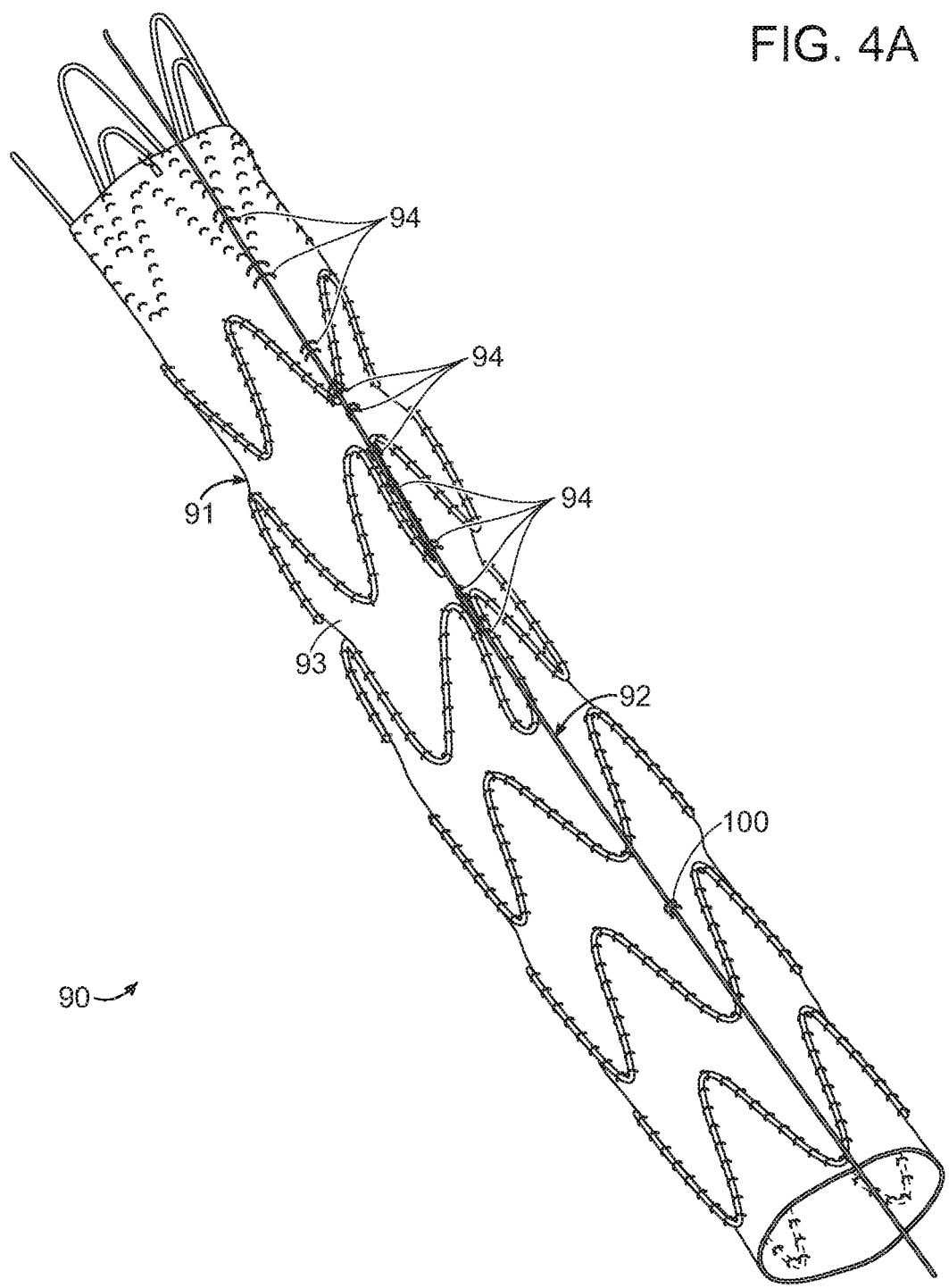
FIG. 4A is a perspective view of a yet another embodiment of the stent graft system of the invention, wherein the ligature is a wire that is sufficiently rigid to maintain a proximal portion of the stent graft prosthesis in a constricted position when the wire extends through suture loops at an outside surface of the stent graft, without requiring that the wire be under tension.
Figure 4B:
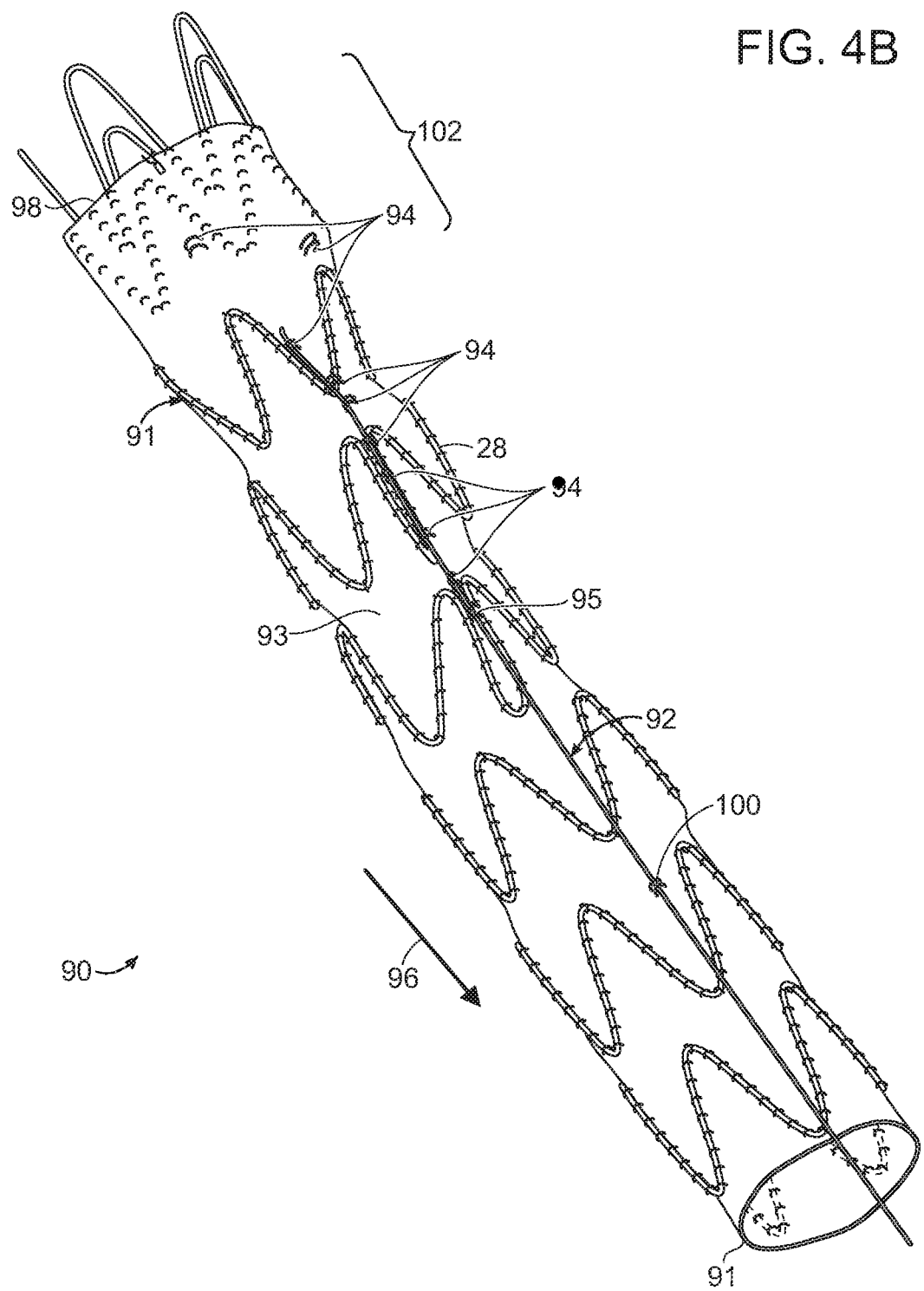
FIG. 4B is a perspective view of the stent graft system shown in FIG. 4A, wherein the wire has been partially retracted from the suture loops at the proximal end of the stent graft, thereby partially releasing the stent graft from radial constriction.
Figure 4C:
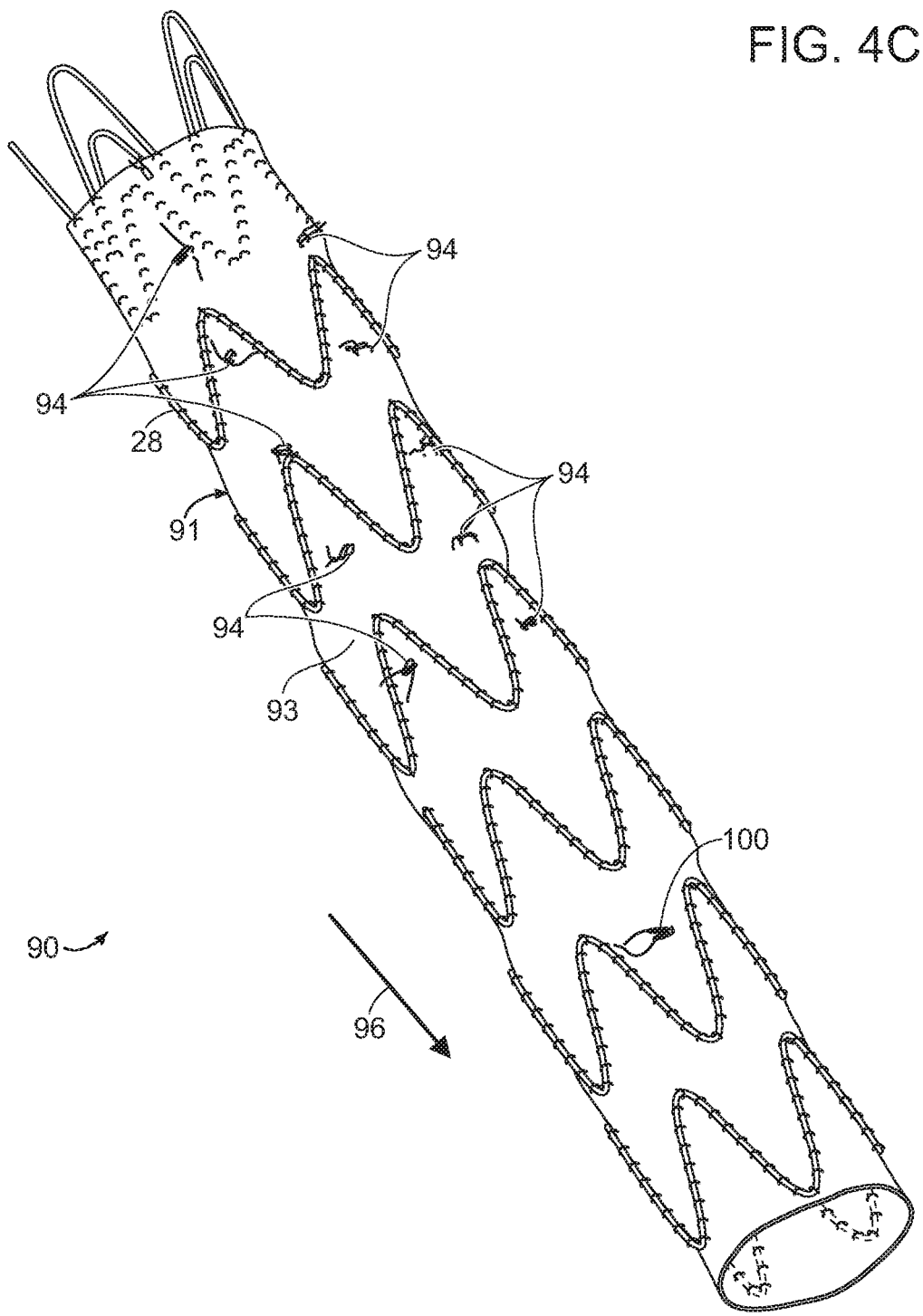
FIG. 4C is a perspective view of the stent graft system of FIGS. 4A and 4B, following complete retraction of the wire from the suture loops radially constricting the stent graft.

In yet another embodiment, shown in FIGS. 4A-4C stent graft system 90 includes stent graft 91. Ligature 92 is sufficiently rigid to cause suture loops 94 to be substantially longitudinally aligned along flexible luminal graft component 93 of stent graft 91 when suture loops 94 are threaded by ligature 92, thereby radially constricting stent graft 91. Stabilizing loop 100 is distal to suture loops 94. An example of a suitable ligature in this embodiment is a wire, for example, materials known to those skilled in the art, such as stainless steel or a shape memory alloy, such as nitinol. As can be seen in FIG. 4B, partial retraction of ligature 92 in a proximal direction indicated by arrow 96 toward the surgeon causes ligature 92 to be retracted from a set of suture loops 94, thereby causing stents 28 proximate to those suture loops to expand from a constricted position to an expanded position, as shown at portion 102 of stent graft 91. Progressive retraction of ligature 92 causes progressive expansion of stents 28 of stent graft 91 from constricted positions to radially expanded positions, accordingly, from proximal end 98 of stent graft 91 progressively through to most-distal suture loop 95, that is sufficiently proximate to another of suture loops 94 to cause at least partial radial collapse of stents 28 when threaded by ligature 92. Complete retraction of ligature 92 from suture loops 94 causes expansion of stent graft 91 from a constricted position to an expanded position, as shown in FIG. 4C.

Figure 5A:
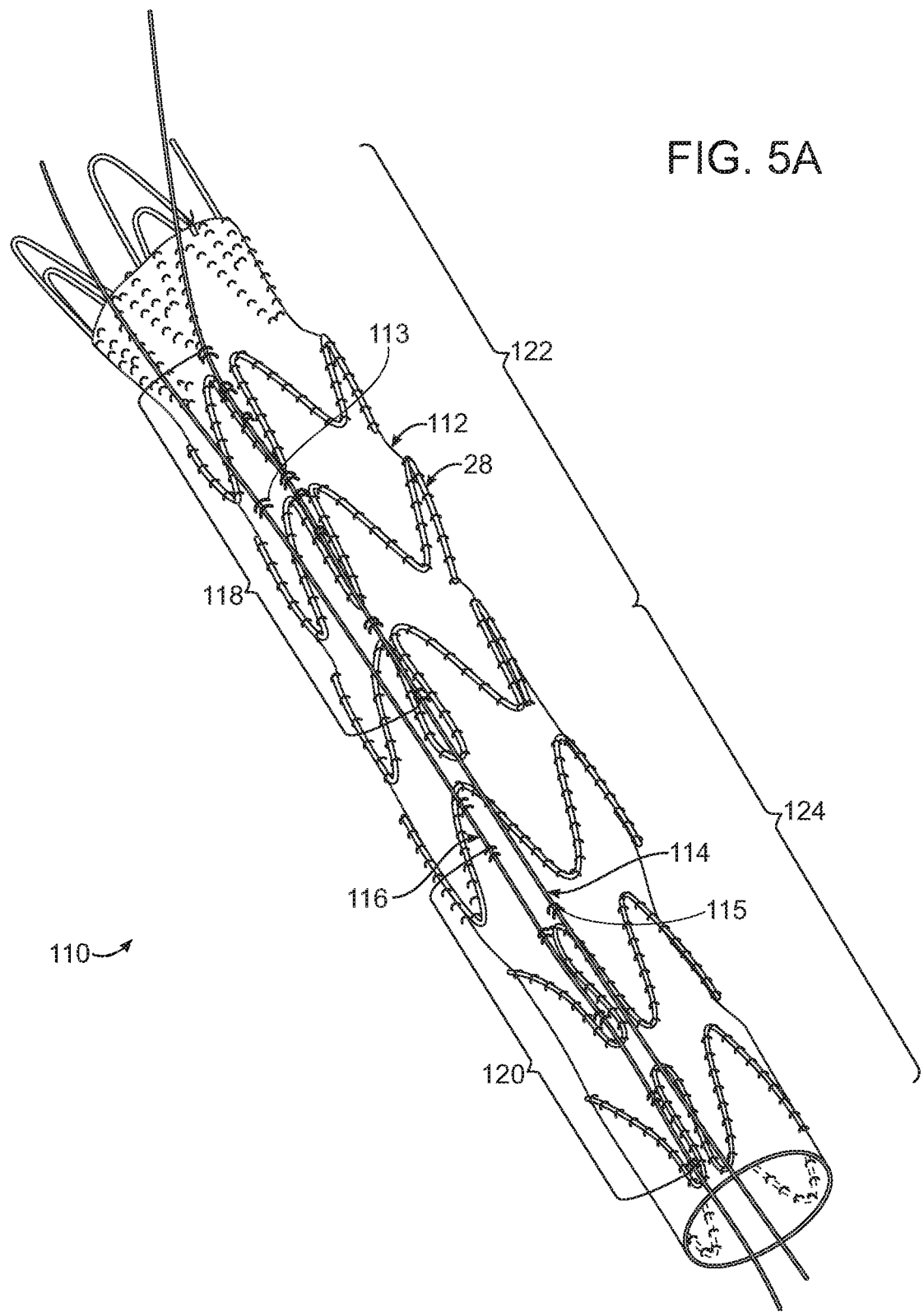
FIG. 5A is a perspective view of still another embodiment of a stent graft system of the invention, wherein two wires extend through separate sets of suture loops, one set of suture loops being at a proximal portion of the stent graft, and the other at a distal portion of the stent graft, thereby radially constricting the stent graft.
Figure 5B:
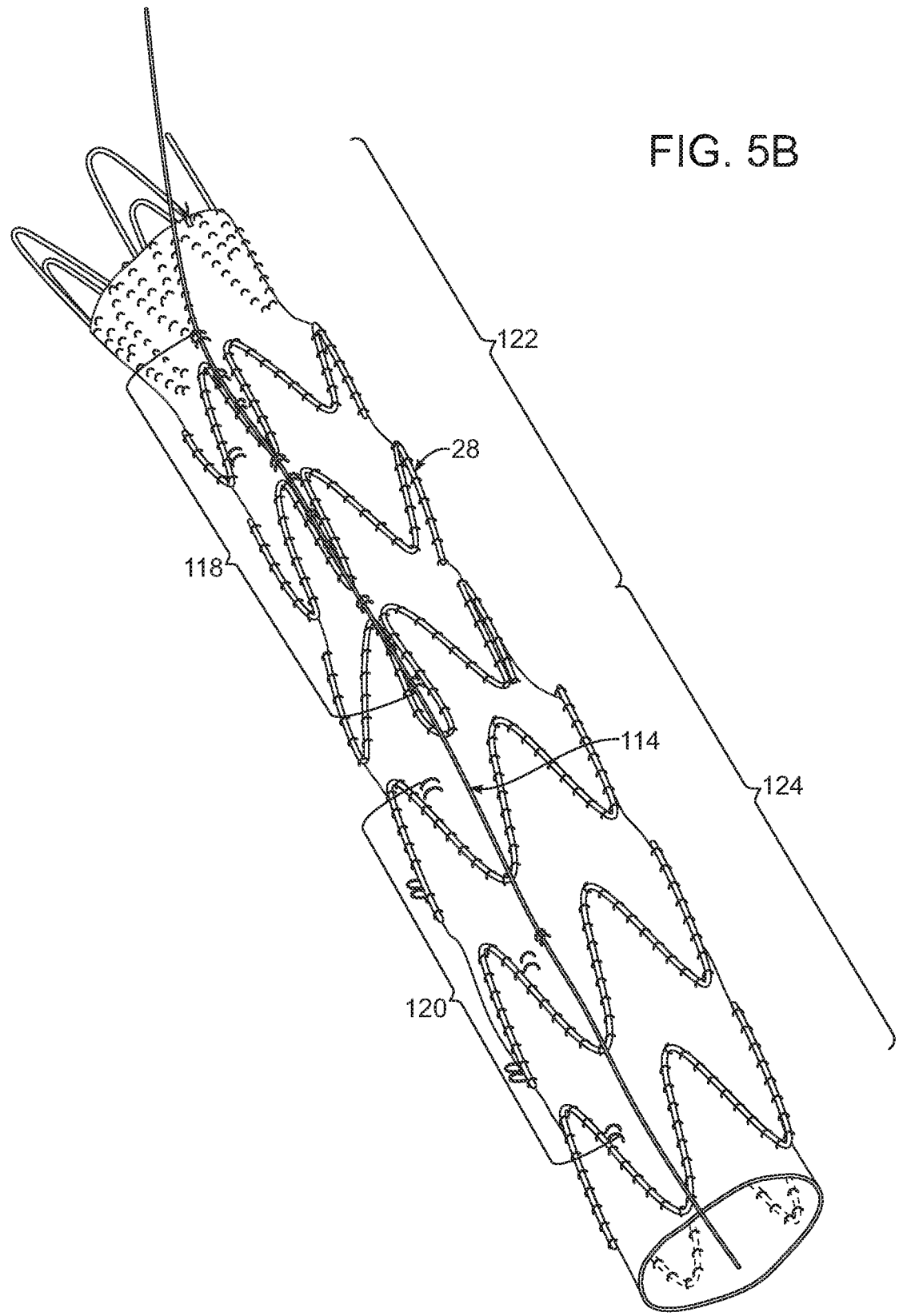
FIG. 5B is a perspective view of the stent graft system of the invention, wherein the wire extending through the set of suture loops at the distal portion of the stent graft has been removed, whereby the distal portion of the stent graft is released from radial constriction.
Figure 5C:
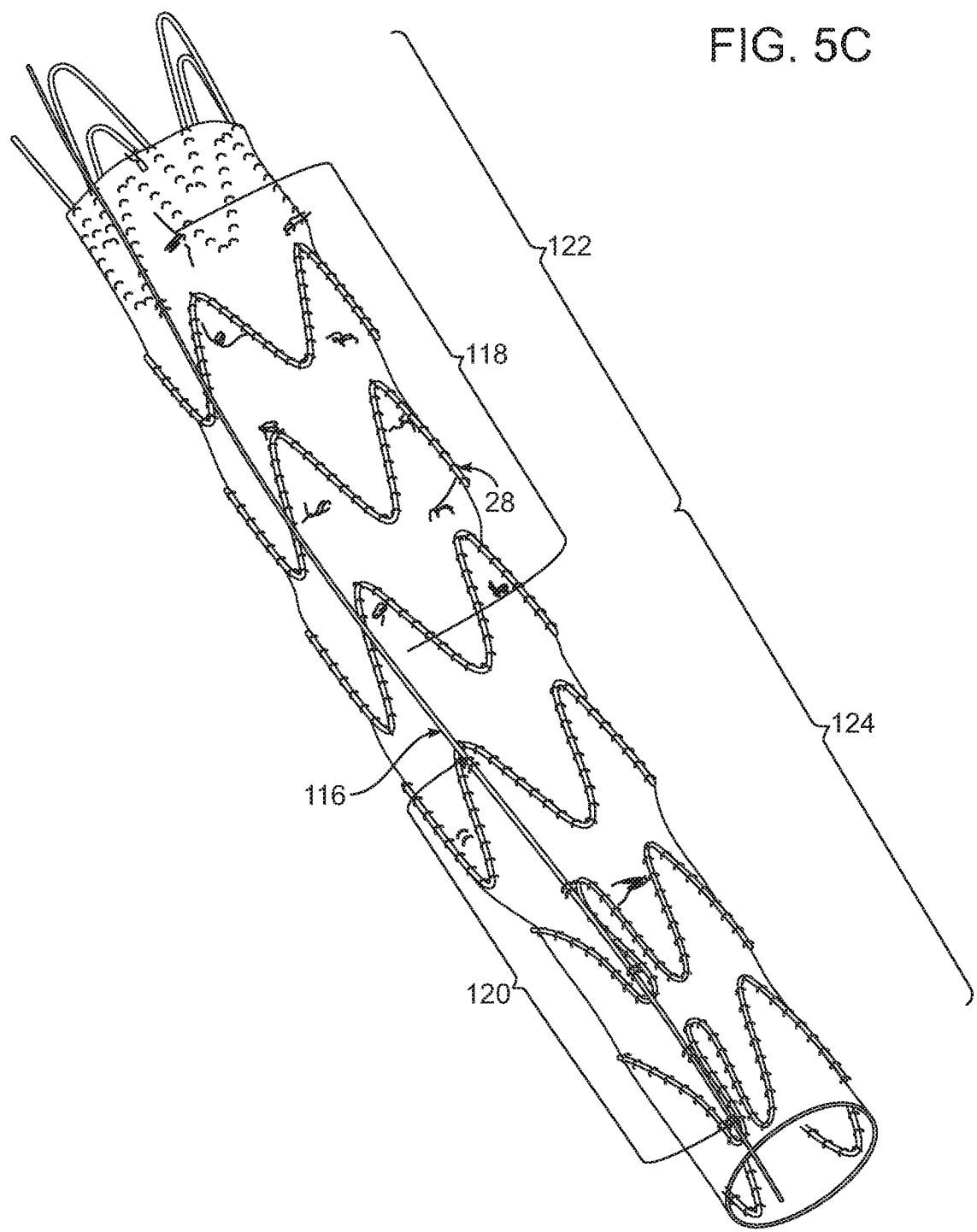
FIG. 5C is a perspective view of the stent graft prosthesis of FIGS. 5A and 5B, wherein the wire extending through the set of suture loops at the proximal portion of the stent graft has been removed, whereby the proximal portion of the stent graft is released from radial constriction.

In another embodiment, shown in FIGS. 5A-5C, stent graft system 110 includes stent graft 112, and two ligatures 114,116 extending through proximal set of suture loops 118 and distal set of suture loops 120, and stabilizing loops 115,113, respectively. As shown in FIG. 5A, stent graft 112 is held in a constricted position along its length by ligatures, such as wires 114,116, extending through proximal and distal sets of suture loops 118,120 distributed predominately at proximal portion 122 and distal portion 124 of stent graft 112, respectively. Ligatures, as shown in FIG. 5A, are wires 114,116, that are sufficiently rigid to constrict stents 28 at proximal set of suture loops 118 and distal set of suture loops 120 threaded by wires 114,116. Selective release of constriction of proximal portion 122 and distal portion 124 of stent graft 112 by independent and selective retraction of wires 114,116 from proximal set of suture loops 118 or distal set of suture loops 120 through which they are threaded. It is to be understood that, ligatures can, independently, be flexible or rigid, or within or outside of stent graft 112, thereby enabling selective constriction or release of proximal portion 122 and distal portion 124 of stent graft 112, as in is shown in FIGS. 5B and 5C.

Another embodiment of a stent graft system of the invention is shown in FIGS. 6A and 6B. As shown therein, stent graft system 10 of FIG. 1 has been modified to stent graft system 10*a*, and includes three ligatures 42, 42*a*, and 42*b* that each extend through separate sets of suture loops 36, 36*a*, and 36*b* distributed at stent graft 12*a* at proximal portion 38 of stent graft 12*a*. In an embodiment, stent graft 12*a* includes fenestration 31 (FIG. 6A(i) and FIG. 6B(i)). Ligature suture loops 36, 36*a*, and 36*b* are distributed along proximal portion 38 of luminal flexible graft component 14 and are distributed radially, laterally and longitudinally relative to each other in an arrangement, as shown in FIG. 6A, and schematically represented in the cross section shown in FIG. 6A(i) taken along line 6A(i)-6A(i) of FIG. 6A. Alignment of ligature suture loops 36, 36*a*, and 36*b*, such as by applying tension on each of ligatures 42, 42*a*, and 42*b*, by moving the proximal ends 44, 44*a*, and 44*b* in the direction of arrow 48, while distal ends 46, 46*a*, and 46*b* are secured relative to the remainder of stent graft system 10*a*. Under tension, stent suture loops 36, 36*a*, 36*b* of each respective ligature 42, 42*a*, and 42*b* become relatively longitudinally aligned, thereby at least partially radially constricting a proximal portion 38 of luminal graft component 14, as shown in FIG. 6B, and as schematically represented in the cross section shown in FIG. 6B(i), taken along line 6B(i)-6B(i) of FIG. 6B. It is to be understood that other arrangements of ligatures about stent graft 12*a* are also possible, such as where instead of three ligatures, along with a fenestration, being evenly distributed about the flexible luminal graft material, only two ligatures may be present and evenly distributed, or only a single ligature or a plurality of ligatures may be present, but unevenly distributed, or variously distributed longitudinally along the stent graft.

FIG. 7 is an exploded side view of another embodiment of a stent graft system of the invention. As shown therein, stent graft system 130 has guidewire catheter 132 that includes proximal end 134 and distal end 136. Nose cone 137 is fixed to distal end 136 of guidewire catheter 132, while proximal handle 138 is fixed to proximal end 134 of guidewire catheter 132. Wires 140,142 each include distal end 144,146 and proximal end 148,150, respectively. Wire handles 152,154 are fixed at proximal ends 148,150 of wires 140,142, respectively. Stent graft 156 includes proximal end 158, distal end 160, stents 162, proximal bare stent 164, and proximal and distal sets of suture loops 166,168 of luminal graft component 170 of stent graft 176. In an embodiment, stent graft 176 includes at least one fenestration 171. Fenestration 171 is defined by luminal graft component 170. Introducer sheath 172 includes distal end 174 and proximal end 176. Distal handle 178 is fixed at proximal end 156 of introducer sheath 170. Wires 140,142 are sufficiently stiff to constrict the radial diameter of stent graft 156 by longitudinally aligning component suture loops of each set of suture loops 166,168 without wires 140,142 being under tension.

FIG. 8A is a side view of the embodiment of a stent graft system 130 shown in FIG. 7, but in assembled form, wherein distal ends 144,146 of ligatures 140,142 have been threaded through proximal set of suture loops 166 and distal set of suture loops 168, respectively, at stent graft 156, and wherein stent graft 156 has been loaded within introducer sheath 172.

In one embodiment of a method of the invention, and as shown in the transition from FIG. 8A to FIG. 8B, stent graft system 130 is directed through an artery of a subject to aneurysm site 180 of the artery, and stent graft 156 is located at and spans aneurysm site 180, having arterial branch 181, as shown. In the embodiment shown, stent graft 156 is exposed by retraction of distal handle 178, in the direction of arrow 182, thereby retracting introducer sheath 172 from stent graft 156, which is held in a radially constricted position by wires 140,142. It is to be understood that, in an alternative embodiment, not shown, stent graft 156, in a radially constricted position, can be directed to aneurysm site 180 by advancement of proximal handle 138 toward distal handle 178, and thereby directing stent graft 156 from within introducer sheath 172 to aneurysm site 180 in the direction indicated by arrow 184 to thereby span aneurysm site 180.

FIG. 8C is a side view of stent graft system 130 shown in FIGS. 8A and 8B, wherein the wire 140, having sufficient rigidity to constrain proximal set of suture loops 166 at proximal portion 158 of prosthesis 156 without being under tension, has been retracted by retraction of wire handle 152 in the direction indicated by arrow 182, thereby allowing stents 162 at proximal portion 158 of stent graft 156 and, therefore, proximal portion 158 of stent graft 156, to radially expand. As described above, where stents 156 are self-expanding, such as self-expanding stents formed of nitinol, withdrawal of wire 140 will cause stent 156 and, consequently, proximal portion 158 of stent graft 156 to selectively radially expand from the constricted direction to an expanded diameter without assistance, such as by use of a balloon catheter.

Alternatively, as shown in FIG. 8D, wire 142, has sufficient rigidity to maintain radially constricted distal portion 168 of stent graft 156 by maintaining distal set of suture loops 168 in a longitudinally aligned position and, therefore, maintain stents 162 at distal portion 160 of stent graft 156 in a radially constricted position. Wire handle 154 is retracted, in the direction indicated by arrow 182, from the position shown in FIG. 8B to that shown in FIG. 8D, while wire handle 152 and wire 140 remain in the position shown in FIG. 8B. As a result, wire 142 is retracted from distal set of suture loops 168, thereby causing stents of stent graft 156 at distal portion 160 of stent graft 156 to radially expand from the constricted position to a radially expanded position, such as by employing radially self-expanding stents or some other technique known in the art, such as use of a balloon catheter (not shown).

FIG. 8E shows stent graft 156 in a radially expanded position, following retraction of both wires 140,142 as a step subsequent to any of the representations shown in FIGS. 8B, 8C, and 8D. Bare stent 164, shown in FIG. 8E, has been released from apex capture device 190 at distal end of guidewire catheter. FIG. 8F is a side view of the stent graft system 130 following full implantation of stent graft 156 at aneurysm 180 including, depending on the presence of arterial branch 181, implantation of branch prosthesis 183, and retraction of the remainder of the stent graft system 130 from aneurysm site 180 and from the subject.

FIG. 9 is an exploded side view of still another embodiment of a stent graft system of the invention. As shown therein, stent graft system 200 has guidewire catheter 202 that includes distal end 204 and proximal end 206. Nose cone 208 is fixed to distal end 204 of guidewire catheter 202. Proximal handle 210 is fixed to proximal end 206 of guidewire catheter. Ligatures are flexible threads 212,214 each having a distal end 216,218 and proximal end 220,222, and wherein control handles 224,226 are fixed to proximal end 220,222 of each thread 212,214, respectively. Stent graft 228 includes proximal portion 230 and distal portion 232. Proximal suture loops 234 and distal suture loops 236 are distributed predominately at proximal portion 230 and distal portion 232 of stent graft 228, respectively. Stents 227 are distributed longitudinally along stent graft 228. Optionally, stent graft 228 defines fenestration 229. Bare stent 252 extends proximally from proximal portion 230. Introducer sheath 238 includes distal end 240 and proximal end 242. Distal handle 244 is fixed to proximal end 242 of introducer sheath 238.

FIG. 10A is a side view of the embodiment of stent graft system 200 shown in FIG. 8, in assembled form. Threads 212,214 extend through respective proximal suture loops 234 and suture loops 236 at stent graft 228 and are fixed at distal end 204 (not shown in FIG. 10A) of guidewire catheter 202. Stent graft 228 (not shown in FIG. 10A) is loaded within introducer sheath 238 and threads 212,214 are held in tension, thereby causing each of proximal suture loops 234 and distal suture loops 236 to be held in an arrangement that constricts the radial diameter of stent graft 228.

In a method of the invention, stent graft system 200 is delivered through an artery to aneurysm site 246 having arterial branch 245. Stent graft 228 spans aneurysm site 246, as shown in FIG. 10B. Introducer sheath 238 is then retracted by directing distal handle 244 in a proximal direction, shown by arrow 248, toward the surgeon, thereby exposing stent graft 228, that is held in a radially constricted position by tension on threads 212,214. It is to be understood that, in an alternative embodiment of the method of the invention, proximal handle 210 can be advanced toward distal handle 244 in a distal direction indicated by arrow 250 to thereby direct stent graft 228, while in a radially constricted position, from distal end 240 of introducer sheath 238 and through an artery to aneurysm site 246 to thereby radially span aneurysm site 250.

In one embodiment of the method, control handle 224 is advanced in distal direction 250, from proximal handle 210 to distal handle 242, as shown in the transition from FIG. 10B to FIG. 10C, to thereby relax thread 212, thereby allowing radially self-expanding stents 227 (or balloon catheter, not shown, within stents 227, as appropriate) at proximal portion 230 of stent graft 228 to radially expand from a constricted position to an expanded position. Alternatively, as shown in the transition from FIG. 10B to FIG. 10D, control handle 224 can remain in a proximal position (FIG. 10B), and control handle 226 can be directed in a proximal direction indicated by arrow 248 to thereby relax thread 214 constraining stents 227 at distal portion 232 of stent graft 228, whereby radially self-expanding stents 227 at distal portion 232 of stent graft 228 radially expand from a constricted position, shown in FIG. 10B, to a radially expanded position, shown in FIG. 10D.

Similarly, as shown in the transition from FIG. 10B to 10E, control handles 224,226 can both be advanced in the direction of arrow 250, thereby relaxing tension on both corresponding threads 212,214, thereby causing proximal suture loops 234 and distal suture loops 236 to relax radial constraint on radially self-expanding stents at both proximal portion 230 and distal portion 232 of stent graft 228, thereby allowing the entirety of stent graft 228 to radially expand from a constricted position, shown in FIG. 10B, to radially expanded position, shown in FIG. 10E. It is to be understood that, in the embodiment represented in FIGS. 10A through 10E, each of the configurations shown can follow or precede any of the other configurations or any configuration in between, due to the radially self-expanding nature of the stents of the prosthesis (or that of a balloon catheter, or catheters), if they are employed simultaneously with release of stent graft 228 from radial constriction by relaxation are increased of tension on either or both of threads 212,214.

This variability enables fine adjustment of stent graft 228 at aneurysm site 246 before it is released from threads 212,214 and guidewire catheter 202.

As shown in the transition from FIG. 10E to FIG. 10F, following rotation and axial alignment of fenestration 229 with branch artery 245, as appropriate or necessary, bare stent 252 is released from capture at nose cone 208 by apex capture device 254, such as is known in the art. Threads 212,214 are then severed from guidewire catheter 202 or nose cone 208 and distal ends 216,218 of threads, by a suitable mechanism, such as by rotating proximal handle 242 and, therefore, guidewire catheter 202 and nose cone 208 relative to control handles 224,226 to thereby sever distal ends 216,218 of threads 212,214 with blades (not shown) integrated within distal end 204 of guidewire catheter 202 or nose cone 208. At this point, stent graft 228 is fully implanted at aneurysm site 246 including, depending on the presence of arterial branch 245, implantation of branch prosthesis 247, as necessary or appropriate, spanning fenestration 229 and branch artery 245, and the remainder of stent graft system 200 that has been severed from stent graft 228 can be retracted from aneurysm site 246 and the patient, as shown in FIG. 10F.

It is also to be understood that, as with the embodiments shown in FIGS. 7 and 8A-8F, threads and wires can be employed in combination, and additional wires with threads can be employed to further improve refinement of control over various portions of the stent graft, such as by employing a third wire, thereby enabling independent control over radial expansion of separate proximal, middle, and distal portions of a stent graft.

Further, stent graft can include a fenestration in the embodiments of the method wherein the stent graft is to be placed at an aneurysm spanning a branch artery. Also, it is to be understood, that as described in earlier embodiments, a ligature, whether wires or threads of the embodiment shown in FIGS. 8, 9A-9F, and 10A-10F can be arranged, independently of each other, to extend within stent graft or outside surface of stent graft.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123; 9,877,857; 9,907,686; U.S. patent application Ser. Nos. 14/575,673; 15/166,818; 15/167,055; 14/272,818; 14/861,479; 15/478,424; 15/478,737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of the "Delivery System For Radially Constricting a Stent Graft and Method of Use," by Eduardo Alejandro Garcia, International Application No. PCT/US2018/019355, filed on Feb. 23, 2018; "Delivery System and Method to Radially Constrict a Stent Graft," by Timothy Lostetter, International Application No. PCT/US2018/019349, filed on Feb. 23, 2018; "Vascular Prosthesis with Moveable Fenestration," by Samuel Arbefeuille, International Application No. PCT/US2018/019353, filed on Feb. 23, 2018; "Stent Graft Delivery System with Constricted Sheath and Method of Use," by Timothy Lostetter, International Application No. PCT/US2018/019354, filed on Feb. 23, 2018; "Stent Graft with Fenestration Lock," by Timothy Lostetter, International Application No. PCT/US2018/019352, filed on Feb. 23, 2018; "Constrainable Stent Graft, Delivery System and Methods of Use," by Samuel Arbefeuille and Nico Bahar, International Application No. PCT/US2018/019342, filed on Feb. 23, 2018; "Vascular Prosthesis with Crimped Adapter and Methods of Use," by Samuel Arbefeuille, International Application No. PCT/US2018/019350, filed on Feb. 23, 2018; "Radially Adjustable Stent Graft Delivery System," by Samuel Arbefeuille, Eduardo Alejandro Garcia and Scott L. Rush, International Application No. PCT/US2018/019356, filed on Feb. 23, 2018; "Vascular Prosthesis with Fenestration Ring and Methods of Use," by Timothy Lostetter, International Application No. PCT/US2018/019351, filed on Feb. 23, 2018; "Distal Torque Component, Delivery System and Method of Using Same," by Samuel Arbefeuille, International Application No. PCT/US2018/019510, filed on Feb. 23, 2018, are also incorporated by reference in their entirety.

While example embodiments have been particularly shown and described, it will be understood by those skilled in the art that various changes in form and details may be made therein without departing from the scope of the embodiments encompassed by the appended claims.

The invention claimed is:

1. A stent graft system, comprising:
 a) a stent graft that includes
  i) a component defining a longitudinally extending outer surface and a longitudinally extending inner surface, the inner surface defining a lumen having a longitudinal axis;
  ii) a plurality of stents distributed longitudinally along the component;
  iii) a plurality of suture loops,
   a first suture loop of the plurality of suture loops spaced both laterally and longitudinally relative to an adjacent suture loop along a first stent of the plurality of stents, when the component is in an expanded configuration; and
 b) at least one ligature having a proximal end and a distal end, the at least one ligature extending through the first suture loop and laterally through the adjacent suture loop, when the component is in an expanded configuration.

2. The stent graft system of claim 1, wherein each suture loop of the plurality of suture loops having a first end and a second end, both the first and second ends attached to the inner surface of the stent graft.

3. The stent graft system of claim 1, wherein each suture loop of the plurality of suture loops having a first end and a second end, both the first and second ends attached to the outer surface of the stent graft.

4. The stent graft system of claim 1, wherein the plurality of suture loops extend around less than an entire circumference of the stent graft.

5. The stent graft system of claim 1, wherein at least a portion of the plurality of suture loops are each nested between an opening of struts of a stent of the plurality of stents.

6. The stent graft system of claim 1, wherein a majority of the plurality of suture loops are closer to a proximal end of the stent graft than a distal end of the stent graft.

7. The stent graft system of claim 1, wherein at least one of the plurality of suture loops is closer to a distal end of the stent graft than to a proximal end of the stent graft.

8. The stent graft system of claim 1, wherein the first suture loop and the adjacent suture loop align longitudinally along a longitudinal axis of the first stent when the first stent is in a radially constricted configuration.

9. The stent graft system of claim 1, wherein the proximal and distal end of the at least one ligature align longitudinally when the component is in a radially constricted configuration.

10. The stent graft system of claim 1, wherein tension on the at least one ligature longitudinally aligns the suture loops along the longitudinal axis of the component, thereby at least partially radially constricting the stent graft.

11. The stent graft system of claim 1, wherein the first stent includes struts joined at opposite ends to define distal and proximal apices, and the first suture loop and the adjacent suture loop are nested between the struts of the first stent.

12. The stent graft system of claim 1, wherein the plurality of stents that are radially constricted by the at least one ligature are radially self-expanding.

13. The stent graft system of claim 1, wherein the component defines a fenestration.

14. The stent graft system of claim 1, wherein each of the plurality of suture loops is a single loop of suture.

15. The stent graft system of claim 1, wherein the at least one ligature comprises a plurality of ligatures,
   a) a first ligature extending through a portion of the plurality of suture loops distributed about a proximal portion of the component,
   b) a second ligature extending through a portion of the plurality of suture loops distributed about a distal portion of the component,
   c) whereby tension of the first ligature independently controls radial expansion of the plurality of stents along the proximal portion of the component, and
   d) whereby tension of the second ligature independently controls radial expansion of the plurality of stents along the distal portion of the component.

* * * * *